«12» United States Patent
Melkonyan et al.

(10) Patent No.: US 8,642,261 B2
(45) Date of Patent: Feb. 4, 2014

(54) GENETIC MARKER FOR DETECTION OF HUMAN PAPILLOMAVIRUS

(75) Inventors: Hovsep S. Melkonyan, Princeton, NJ (US); Natalya Ossina, legal representative, Princeton, NJ (US); Samuil R. Umansky, Princeton, NJ (US); Zhenghan Xin, Newtown, PA (US)

(73) Assignee: Trovagene, Inc., San Diego, CA (US)

( * ) Notice: Subject to any disclaimer, the term of this patent is extended or adjusted under 35 U.S.C. 154(b) by 228 days.

(21) Appl. No.: 13/126,081

(22) PCT Filed: Oct. 26, 2009

(86) PCT No.: PCT/US2009/062114
§ 371 (c)(1),
(2), (4) Date: Aug. 31, 2011

(87) PCT Pub. No.: WO2010/051261
PCT Pub. Date: May 6, 2010

(65) Prior Publication Data
US 2011/0318727 A1    Dec. 29, 2011

Related U.S. Application Data

(60) Provisional application No. 61/197,850, filed on Oct. 31, 2008.

(51) Int. Cl.
*C12Q 1/68* (2006.01)

(52) U.S. Cl.
USPC ......... 435/6.1; 435/6.11; 435/91.2; 536/22.1; 536/23.1; 536/24.3

(58) Field of Classification Search
USPC ............... 435/6.1, 6.11, 61.2, 91.2; 536/22.1, 536/23.1, 24.3
See application file for complete search history.

(56) References Cited

U.S. PATENT DOCUMENTS 4,983,728 A * 1/1991 Herzog et al. .................... 435/5

* cited by examiner

*Primary Examiner* — Ardin Marschel
(74) *Attorney, Agent, or Firm* — Patentique PLLC

(57) ABSTRACT

The invention provides compositions and methods for the differential detection of high risk forms of HPV from a urine sample provided by a patient. Specifically, the invention provides primers and probes that specifically recognize and bind sequences within the E1 gene of HPV. Detection of high risk forms of HPV identify individuals at risk of developing or in the early stages of cervical carcinoma.

25 Claims, 5 Drawing Sheets

GENETIC MARKER FOR DETECTION OF HUMAN PAPILLOMAVIRUS

RELATED APPLICATIONS

The present application is a 35 U.S.C. §371 National Phase Application of PCT/US2009/062114, filed Oct. 26, 2009, which claims priority to, and the benefit of, U.S. Provisional Application No. 61/197,850, filed Oct. 31, 2008. The contents of these applications are herein incorporated by reference in their entirety.

INCORPORATION-BY-REFERENCE OF SEQUENCE LISTING

The contents of the text file named "29480-512N01US_ST25.txt", which was created on Aug. 26, 2011 and is 25 KB in size, are hereby incorporated by reference in their entirety.

FIELD OF INVENTION

This invention relates to the fields of medicine and molecular biology. More specifically, the invention relates to use of the E1 gene fragment of papillomavirus genome as a specific marker for differential diagnosis by detection of most common high risk HPV genotypes against low risk counterparts

BACKGROUND OF THE INVENTION

According to the latest global estimates, 493,000 new cases of cervical cancer occur each year among women, and 274,000 women die of the disease annually (Jacques Ferlay et al., 2002, *GLOBOCAN*). Because the disease progresses over many years, an estimated 1.4 million women worldwide are living with cervical cancer, and two to five times more, or up to 7 million women worldwide, may have precancerous conditions that need to be identified and treated (Ferlay et al. 2002, *GLOBOCAN*; Bosch et al. 2002, J Clin Pathol. 55: 244-265). The lack of effective screening and treatment strategies is a major reason for the significantly higher cervical cancer rates in developing countries compared with developed countries.

Screening efforts have relied largely on the Pap smear, a laboratory test developed in the 1940s to detect abnormal cervical cells. The test has achieved tremendous success in industrialized countries that offer periodic, high-quality screening. But Pap smear programs are complex and costly to run and have failed to reach a significant proportion of women in developing countries where health systems and infrastructure are weak Importantly, in some countries women do not perform or consent to the Pap smear procedure due to cultural restrictions. Furthermore, there are analytical problems associated with Pap smear test. Pap smear does not detect all cases of cervical dysplasia or premalignancy. The current acceptable rate for false negatives for a test that guides physician to make a medical recommendation is approximately 5-10% but recent studies suggest that the actual rate of Pap smear may be much higher (Nanda K. et al., 2000, *Ann Intern Med.* 132: 810-819; Kulasingam S. et al., 2002, JAMA. 288:1749-1757). The Pap smear defines approximately 7-8% of cases as atypical squamous cells of undetermined significance (AS-CUS). In an additional 20-30% of cases, the Pap smear may be insufficient for interpretation due to the presence of inflammatory cells. Currently, to overcome shortcomings associated with the Pap smear test more studies are underway for developing new analytically more reliable assays for early detection of cervix premalignant condition in women. One of the approaches, based on universally accepted connection between consistent HPV infection of cervix and development of invasive cervical cancer is directed to the detection of the virus.

SUMMARY OF THE INVENTION

The invention provides compositions and methods for differential detection of the high risk type HPV. Specifically, a newly identified fragment of HPV genome is used as a marker for this differential detection of the high risk type viruses. Oligonucleotide primer and probe compositions that target this marker fragment are used to detect high risk HPV in clinical samples such as urine.

Specifically, the invention provides a composition including an isolated genetic marker for human papillomavirus (HPV) including the sequence encoded by SEQ ID NO: 69, 70, 71, 72, 73, 74, 75, 76, 77, 78, 79, 80, 81, 82, 83, 84, 85, 86, 87, 88, 89, 90, 91, 92, 93, 94, 95, 96, or 97. Alternatively, or in addition, the invention provides a composition including the complementary sequence of SEQ ID NO: 69, 70, 71, 72, 73, 74, 75, 76, 77, 78, 79, 80, 81, 82, 83, 84, 85, 86, 87, 88, 89, 90, 91, 92, 93, 94, 95, 96, or 97. In a preferred aspect, the invention provides a composition including an isolated genetic marker for high-risk human papillomavirus (HPV) containing the sequence encoded by SEQ ID NO: 69, 70, 71, 72, 73, 74, 75, 76, 77, 78, 79, 80, 81, 82, 83, 84, or 85.

The invention further provides a composition including an oligonucleotide encoded by the sequence by SEQ ID NO: 1, 2, 3, 4, 5, 6, 7, 8, 9, 10, 11, 12, 13, 14, or 15. Alternatively, or in addition, the invention provides a composition including the complementary sequence of SEQ ID NO: 1, 2, 3, 4, 5, 6, 7, 8, 9, 10, 11, 12, 13, 14, or 15.

Moreover, the invention provides a composition including an isolated genetic marker for human papillomavirus (HPV) including a sequence homologous to the E1 gene of HPV. In one aspect, the sequence includes nucleotides 987 to 1135 of the E1 gene of HPV. In another aspect, the sequence is encoded by SEQ ID NO: 69, 70, 71, 72, 73, 74, 75, 76, 77, 78, 79, 80, 81, 82, 83, 84, 85, 86, 87, 88, 89, 90, 91, 92, 93, 94, 95, 96, or 97. The invention encompasses a sequence that is at least 50%, 55%, 60%, 65%, 70%, 75%, 80%, 85%, 90%, 95%, 100%, or any percentage point in between, identical to the E1 gene of HPV. In a preferred embodiment, the sequence is at least 70% identical to the E1 gene of HPV. The invention encompasses a sequence that is at least 50%, 55%, 60%, 65%, 70%, 75%, 80%, 85%, 90%, 95%, 100%, or any percentage point in between, homologous to the E1 gene of HPV. In a preferred embodiment, the sequence is at least 70% homologous to the E1 gene of HPV.

The invention provides a method of diagnosing a human papillomavirus (HPV) infection in a patient, including the steps of: (a) obtaining a urine sample from said patient; and (b) detecting one or more sequences of the E1 gene of HPV in said urine sample; wherein detecting one or more sequences of the E1 gene of HPV indicates that presence of at least one human papillomavirus, thereby diagnosing an HPV infection in a patient. According to this method, the nucleic acids are DNA or RNA. In a preferred embodiment of this method, the DNA is transrenal DNA. This method detects HPV DNA that comprises transrenal DNA. Alternatively, this method detect transrenal DNA, exclusively.

In certain embodiments of this method, the detecting step includes a technique selected from the group consisting of hybridization, polymerase chain reaction (PCR); nested primer PCR; Real Time PCR; NA hybridization; Cyclic Probe Reaction; Single-Strand Conformation Polymorphism (SSCP); Strand Displacement Amplification (STA); and Restriction Fragment Length Polymorphism (RFLP).

The detecting step includes a polymerase chain reaction that uses primer pairs sufficiently complementary to hybridize with a sequence in the E1 gene of HPV. Moreover, the detecting step includes a polymerase chain reaction that uses primer pairs sufficiently complementary to hybridize with a sequence encoded by SEQ ID NO: 69, 70, 71, 72, 73, 74, 75, 76, 77, 78, 79, 80, 81, 82, 83, 84, 85, 86, 87, 88, 89, 90, 91, 92, 93, 94, 95, 96, or 97. Alternatively, or in addition, the detecting step includes a polymerase chain reaction that uses primer pairs sufficiently complementary to hybridize with a sequence encoded by SEQ ID NO: 1, 2, 3, 4, 5, 6, 7, 8, 9, 10, 11, 12, 13, 14, or 15, or a complementary sequence thereof. When the methods described herein use a polymerase chain reaction (PCR)-based method to detect HPV, the polymerase chain reaction uses the primer pair of SEQ ID NO: 41 and 42. The primer pair of SEQ ID NO: 41 and 42 differentially detects high-risk forms of HPV. Alternatively, the polymerase chain reaction uses at least one of the following primer pairs encoded by SEQ ID NOs: 43 and 55, 44 and 56, 45 and 30, 46 and 57, 47 and 58, 48 and 33, 49 and 34, 50 and 36, 51 and 59, 52 and 38, 53 and 39, or 54 and 40. In certain embodiments, the polymerase chain reaction uses at least one forward primer selected from the group consisting of SEQ ID NOs: 43, 44, 45, 46, 47, 48, 49, 50, 51, 52, 53, and 54, and at least one reverse primer selected from the group consisting of SEQ ID NOs: 55, 56, 30, 57, 58, 33, 34, 35, 36, 59, 38, 39, and 40. The polymerase chain reaction further uses at least one of the following primer pairs encoded by SEQ ID NOs: 43 and 55, 44 and 56, 45 and 30, 46 and 57, 48 and 33, 50 and 36, 51 and 59, and 52 and 38. In certain aspects, the polymerase chain reaction uses at least one forward primer selected from the group consisting of SEQ ID NOs: 43, 44, 45, 46, 47, 48, 49, 50, 51, 52, and 54, and at least one reverse primer selected from the group consisting of SEQ ID NOs: 55, 56, 30, 57, 58, 33, 35, 36, 59, 38, and 39.

In certain embodiments of the invention, multiple pairs of primers are added to a PCR reaction contained in single tube. Group PCR reactions include 1-5, 5-10, 10-15, 15-20, 20-25 primers, or any number in between. Group PCR reactions are used to identify all possible forms of HPV that are present in a biological or clinical urine sample. For example, the primers listed in Table 3, Table 4, or Table 5 are applied to any given sample in the context of a single PCR reaction.

According to certain aspects of this method, nucleic acid degradation in said urine sample is reduced. Reducing nucleic acid degradation includes inhibiting nuclease activity by increased pH, increased salt concentration, heat inactivation, or by treating said urine sample with a compound selected from the group consisting of ethylenediaminetetraacetic acid, guanidine-HCl guanidine isothiocyanate, N-lauroylsarcosine, and sodium dodecylsulphate.

The detecting step of this method further includes substantially isolating said nucleic acids in said urine sample. Isolation is performed by precipitation or by using a solid adsorbent material.

This method further comprises filtering the urine sample to remove contaminants. In one aspect, filtering removes nucleic acids comprising more than about 1000 nucleotides. In another aspect, filtering removes nucleic acids comprising more than about 300 nucleotides.

Additionally, this method further includes the step of quantifying said nucleic acids. Quantification is accomplished by methods known in the art.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and not intended to be limiting.

Other features and advantages of the invention will be apparent from the following detailed description and claims.

DETAILED DESCRIPTION

Figure 1:
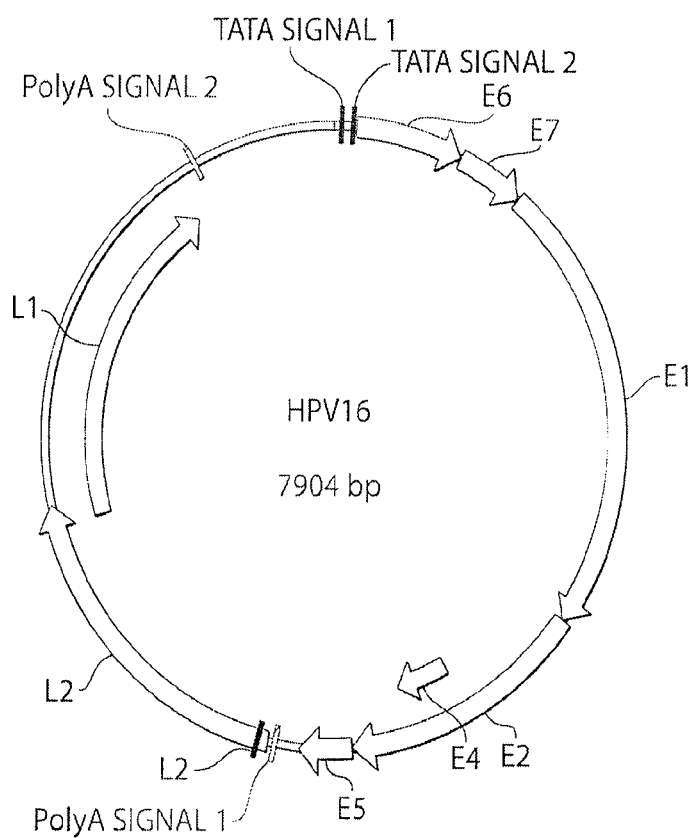
FIG. 1 is a schematic diagram, or map, of the Open Reading Frames (ORFs) in the genome of HPV16.

Human papillomaviruses (HPVs) are epitheliotropic viruses associated with benign and malignant lesions of cutaneous and mucosal epithelia (FIG. 1 for the genetic map of the virus).There is well documented causative connection between HPV infection and subsequent development of cervical cancer. There are also observations associating HPV infection with cancers of the head and neck, respiratory tissue and breast. (Braakhuis et al., 2004, J. Natl. Cancer Inst. 96(13): 998-1006; Dahlstrand et al., 2004, Anticancer Res. 24(3b): 1829-35; Daling et al., 2004, Cancer 101 (2): 270-80; Ha et al., 2004, Crit. Rev. Oral Biol. Med. 15(4): 188-96; Hafkamp et al., Acta Otolaryngol. 124(4): 520-6; Harwood et al., 2004, Br. J. Dermatol. 150(5):949-57; Rees et al., 2004, Clin. Otolaryngol. 29(4):301-6; Widschwendter et al., 2004, J. Clin. Virol. 31(4):292-7).

More than 100 different types of HPV have been identified to date (Antonsson, A., et al., 2000, J. Virol. 74:11636-11641; Chan, S. Y., et al. 1995, J. Virol. 69:3074-3083; de Villiers, E. M.,et al. 2004, Virology 324:17-27), of which 40 have been reported in anogenital infections (de Villiers E-M. 2001, Papillomavirus Rep. 12:57-63; Villiers EM et al., 2004, Virology. Jun 20;324(1):17-27). Based on epidemiologic classification of HPV there are 15 high-risk and 5 low-risk viral genotypes (Munoz N et al., 2003, N Engl J Med., 348, 518-527). It is accepted that nearly 100% of invasive cervical cancers and high-grade precancerous intraepithelial neoplasias are associated with infection by high-risk HPV infection. This is the rational for the use of high-risk HPV detection for screening of women and identification of individuals at risk for subsequent development of cervical cancer.

As HPV cannot be cultured in vitro and serological assays are still ineffective, diagnosis of HPV infection is based on the use of molecular tools. Direct dot-spot detection and in situ hybridization assays have been described (Melchers W J, et al., 1988, J Med Virol 25:11-16; Melchers W J, 1989, J Clin Microbiol, 27:106-110) but these methods are tedious and appear to lack sensitivity and specificity. DNA amplification methods, such as the polymerase chain reaction (PCR), permit more sensitive detection of the viral DNA. Besides type-specific PCR primers for individual HPV genotypes (Baay MF, et al., 1996, J Clin Microbiol, 34:745-747; van den Brule A J, et al., 1989, J Med Virol, 29:20-27) several universal PCR primer sets have been developed, including MY11/MY09 (Manos MM, et al., 1989, Cancer Cells, 7:209-214) OBI/II (Jenkins A, et al 1991, APMIS, 99:667-673) CPI/CPIIG (Tieben LM, et al., 1993, J Virol Methods, 42:265-279), GP5+/6+(de Roda Husman AM, et al., 1995, J Gen Virol, 76:1057-1062), SPF primers (Kleter B, et al., 1998, Am J Pathol. Dec; 153(6): 1731-9) and HP primers derived from SPF primers (Payan C, et al., 2007, J Clin Microbiol., 45(3):897-901). All these primers were aimed at the detection of all HPV subtypes with subsequent differentiation of high risk types from low risk using specific probes. Similarly, there are numerous issued patents disclosing primers and probes for the detection of HPV in clinical specimens (U. S. Pat. No. 6,583,278, June, 2003, Carter; N. M. (E6 and E7); U. S. Pat. No. 6,503,704, January, 2003, Mahony, et al. (L1); U. S. Pat. No. 6,355,424, March, 2002, Lorincz, et al.; U. S. Pat. No. 6,228,577, May, 2001, Mahony, et al.; U. S. Pat. No. 6,218,104, April, 2001, Morris, et al.; U. S. Pat. No. 6,045,993, April, 2000, Mahony, et al.; U. S. Pat. No. 5,888,724, March, 1999, Silverstein, et al.; U. S. Pat. No. 5,783,412, July, 1998, Morris, et al.; U. S. Pat. No. 5,705,627, January, 1998, Manos, et al.; U. S. Pat. No. 5,639,871, June, 1997, Bauer, et al.; U. S. Pat. No. 5,527, 898, June, 1996, Bauer, et al.; U. S. Pat. No. 5,447,839, September, 1995, Manos, et al.; U. S. Pat. No. 5,283,171, February, 1994, Manos, et al.; U. S. Pat. No. 5,182,377, January, 1993, Manos, et al.; U. S. Pat. No. 5,501,947, March, 1996, Emery, et al).

The invention provides primers and probes that detect HPV in all modalities: (i) direct detection of the most frequent high risk types only using nucleic acid (NA) amplification or other analytical methods, (ii) direct detection of the most frequent high risk types using a two step process (NA amplification with a subsequent analysis of the product by hybridization) and (iii) amplification and analysis of high and low risk HPV types in a single reaction. The invention further provides methods for the design and use of oligonucleotide primers specific for E1 gene region of HPV. Critically, the compositions and methods of the invention address a long-felt need for detection, screening and monitoring of diseases associated with HPV infection.

One of the shortcomings of currently available tests for HPV screening is the source of DNA, namely cervical cells. Collection of cervical cells from a patient requires a visit to a doctor's office and at least a trained technician, but more likely, a certified physician, to perform the specimen collection. Moreover, the procedure is invasive and uncomfortable for the patient. It is suggested that the preceding obstacles to collection of cervical cells could be the reason that around 30% of women in United States do not have Pap smear examinations on a regular basis (Ackermann S P, et al., 1992, MMWR CDC Surveill Summ, 41: 17-25; Anderson, L M, May D S. 1995, Am J Public Health, 85: 840-2). Further, there are religious and other cultural reasons limiting women's visit to the gynecologist office for cervical sampling and general vaginal examination.

The invention provides a solution to address above-mentioned obstacles to cervical cell collection. The methods of the invention use a different source of HPV DNA, which does not require cervical scrapings. Rather, the compositions and methods of the invention detect HPV DNA in a urine sample obtained from a patient. HPV DNA is detected in the cellular pellet of centrifuged urine (Payan C, et al., 2007, J Clin Microbiol., 45(3):897-901; Forslund O, et al.,1993, J Clin Microbiol., 31(8):1975-9; Song E S, et al., 2007, J Korean Med Sci., 22(1):99-104) or whole urine (50, 51, 52 Brinkman J A, et al., 2002, J Clin Microbiol., 40(9):3155-61; Sellors J W, et al., 2000, CMAJ. 163(5):513-8; Smits P H, et al., 2005, J Clin Microbiol. 2005, 43(12):5936-9). However, the preceding published tests are PCR based. Clinical sensitivity in these reports is not satisfactory due to the size of amplimers that ranged from 100 to 500 base pairs (bp).

Currently, it is accepted in the art that NA appear in urine from two sources, (i): cells shed into urine from genitourinary tract, of NAs of which are usually high molecular weight, and (ii): transrenal NAs (Tr-DNA) that cross the kidney barrier from the bloodstream into urine, which are usually low molecular weight fragments. Low molecular weight transrenal NA sizes range from about 20 to 150 by (Chan K C, et al., 2008, Clin Cancer Res., 14(15):4809-13; Su Y H, et al.,2004, Ann N Y Acad Sci., 1022:81-9; Umansky S R, Tomei L D. 2006, Expert Rev Mol Diagn., 6(2):153-63). Reduction of amplicon size increases test sensitivity by 10-fold (Melkonyan H S, et al., 2008, Ann. N.Y. Acad. Sci. 1137: 73-81). Therefore, the invention provides methods for the design and use of oligonucleotide primers that target very short (about 30 to 50 bp) amplicon. Oligonucleotide primer compositions of the invention effectively detect both HPV DNA released from cells that are shed as well as Tr-DNA in urine.

Critically, Oligonucleotide primer compositions of the invention target a newly identified highly specific genetic marker in the E1 gene of HPV (Table 1). Targeting this marker within the E1 gene allows the design of PCR primers and probes for specific detection of high risk HPV genotypes in a clinical or biological sample. The invention also provides high risk HPV specific primers mapped to an area of the E1 gene that amplify very short DNA fragments to detect HPV genome fragments present in the Tr-DNA fraction of urine.

Oligonucleotides selected from the regions of the E1 gene of HPV specified in Table 1, or complementary sequences are used for HPV detection in a biological or clinical sample.

Moreover, an oligonucleotide or complementary sequence with at least 50%, 55%, 60%, 65%, 70%, 75%, 80%, 85%, 90%, 95%, 100% homology or identity, or any percentage point in between is used for HPV detection in biological or clinical sample. HPV is detected from a biological or clinical sample using the following exemplary techniques, including, but not limited to, polymerase chain reaction (PCR) and all variants of this method; Real Time PCR; NA hybridization; Cyclic Probe Reaction; Single-Strand Conformation Polymorphism (SSCP); Strand Displacement Amplification (STA); Restriction Fragment Length Polymorphism (RFLP), and techniques of NA analysis involving nanotechnology. Primers may hybridize to binding sites which are either immediately adjacent to each other on the target sequence or slightly overlapping (having no intervening sequences between the primer binding sites).

Further, oligonucleotides selected from regions of the E1 gene of HPV (provided in Table 1), detect specific RNA transcripts of E1 gene by a reverse transcription PCR reaction. Biological and clinical samples of the invention include, but are not limited to, any fluid in the body including blood, urine, saliva, sputum, tears, semen, milk, or vaginal secretions. In a preferred embodiment of the invention, the biological or clinical sample is urine.

Further encompassed by the present invention is a diagnostic kit for detecting HPV, comprising: reagents to facilitate the isolation of DNA of 20-500 nucleotides in length from urine; reagents to facilitate amplification of DNA of 20-500 nucleotides in length by the polymerase chain reaction; a heat stable DNA polymerase; and an oligonucleotide specific for a marker sequence only occurring in the E1 gene of HPV.

TABLE 1

Multiple Alignment of DNA sequences of part of E1 gene for high and low risk HPV genotypes

```
SEQ
ID
NO:          10        20        30        40        50        60        70
       ....|....|....|....|....|....|....|....|....|....|....|....|....|....|....
 69    cagtgatacaggtgaa---gatttggtagattttatagtaaatgataatgattatttaacacaggcagaaacagagaca
 70    aacagacacagggtcg---gatatggtagattttattgatacacaaggaacattttgtgaacaggcagagctagagaca
 71    tagtgatactggggag---gatatggttgactttattgacaattgtaatgtatacaacaatcaggcagaagcagagaca
 72    agatgacagtggcacg---gatttactagagtttatagatgattctatggaaaatagtatacaggcagacacagaggca
 73    ctgtgacaggggggag---gatatggtggactttataaatgatacagatatattaaacatacaggcagaacagagaca
 74    aacagatacaggttca---gacctggcagactttattgatgattccacagatatttgtgtacaggcagagcgtgagaca
 75    aacagatacagggtcg---gatatggtagattttattgacacacaattatccatttgtgaacaggcagagcaagagaca
 76    agatgatacaggatct---gatttaataaactttatagatagtgaaactagtatttgcagtcaggcggaacaggagaca
 77    atatgatagtggaaca---gatctaatagattttatagatgattcaaatataaataatgaacaggcagaacatgaggca
 78    ggatgaaatagataca---gatttagatggatttatagacgattcatatatacaaaatatacaggcagacgcagaaaca
 79    agacgatagtggtaca---gatttaatagagtttatagatgattcagtacaaagtactacacaggcagaagcagaggca
 80    aacagatacaggttca---gacttggtagattttattgatgataccacaacaatttgtgtacaggcagagcgcgagaca
 81    aaatgatacagggtct---gatataatagactttatagatacaaataacagtatttgcagtcaggcggaacaagagaca
 82    gaatgaaacagataca---gatgtagatggatttatagacaatacacttataaacaatacacaggaagacagggagaca
 83    aacagatacaggttca---gacatggtagattttgatgattctacacatatttgtatacaggcagagcgtgagaca
 84    aagc---accgaatct---gatttggatgggtttatagacaatagtaatataatatctacacaggcagaaagggagaca
 85    aggggatacagatgagtcggaaatgggggattttattgataatgcacatataccaaatatatgcacaacaggaaatt
 86    ggtggaggacagtgggtatgacatggtggactttattgatgacagcaatattacacacaattcactggaa---------
 87    ggtggaggacagtgggtatgacatggtggactttattgatgacagcaatattacacacaattcactggaa---------
 88    agtggaggatagtgggttggatatggtggactttatagatgacaggcctattacacacaattccatggaa---------
 89    agagga---tagtggatttgatatgatagattttattgataatagtgttgtggcagaggaacatgtagaactaagtaat
 90    agaggaagatagtgggtttgatatggtggactttttaataata---cattagaagacagttgtacagaccacagcagt
 91    tgtagacgatagtgggttagatcttgtggattttgtagataatagtacagtaatacataacaaagcaggtac------at
 92    ---ggaggacagtgggcttgatatggtggactttattgataatagtgtgtcacaggtagaggggcaggaa------aat
 93    ---cattgacacagggggaagacctagtagacttcatagatacaaggcgcccgggggatgggcaggaagtgc--------
 94    aacagatacaggttca---gacttggcagactttattgatgatactacagatatttgtgtacaggcagagcgcgagaca
 95    ---tgaggacaggggagagatctggtgactttatagacacaagatccttaggggatgggcaggaagtgc--------
 96    ---tgcagatacaggagaggatctagtagatttcatagatacacgatatccaggggatgggcaggaagtgc--------

SEQ
ID
NO:    80        90        100       110       120       130       140       150
       ....|....|....|....|....|....|....|....|....|....|....|....|....|....|...
 69    gcacatgcgttgtttactgcacaggaagcaaaacaacatagagatgcagtacaggttctaaaacgaaagtattt
 70    gcacaggcattgttccatgcgcaggaggtccacaatgatgcacaagtgttgcatgttttaaaacgaaagtttgc
 71    gcacaggcattgtttcatgcacaggaagcggaggaacatgcagaggctgtgcaggttctaaaacgaaagtatgt
 72    gcccgggcattgtttaatatacaggaaggggaggatgatttaaatgctgtgtgtgcactaaaacgaaagtttgc
 73    gcacaagcattatttcatgcacaggaggagcaaacacacaaagaggctgtacaggtcctaaaacgaaagtatgc
 74    gcacaggtacttttacatatgcacaaggcccaaaggcagtagcacagtgcgtgcctaaaacgaaagtatac
 75    gcacaggcattgttccatgcgcaggaagttcagaatgatgcacaggtgttgcatctttttaaaacgaaagtttgc
 76    gcacgggcgttgtttcaggcccaagaattacaggcaaacaaagaggctgtgcatcagttaaaacgaaagtttct
 77    gcccgggcattgtttaatgcacaggaaggggagatttacatgctgtgtctgcagtaaaacgaaagtttac
 78    g-tcaacaattgttgcaagtacaaacagcacatgcagataaacagacgttgcaaaaactaaaacgaaagtatat
 79    gcccgagcgttgtttaatgtacaggaagggtggacgatataaatgctgtgtgtgcactaaaacgaaagtttgc
 80    gcacaggccttgtttaatgtgcaggaagcccaaagggatgcacgggaaatgcatgttttaaaacgaaagtttg-
 81    gcacgggcgttgtttcaggtccaagaaacacaggcacacaaagaggctgcacagcatctaaaacgaaagttttt
 82    gctcaacaattattgcaagtacaaacagcacatgcagatgcacagacgttgcaaaaactaaaacgaaagtatat
 83    gcacaggtacttttgaatatgcaagaggcccaaagggatgcacaagggtgcgtgccctaaaacgaaagtatac
 84    gctcagcagttgttacatgccaaaaca-cacatgcagatacacagacgctgcagaaattaaaacgaaagtattt
 85    gcacaggcattgtatcagtcacagcaagcaaatgcagacaatgaggctatacgtgttctaaaacgaaagtttac
 86    gcacaggcattgtttaacaggcaggaggcggacacccattatgcgactgtgcaggacctaaaacgaaagtatt
 87    gcacaggcattgtttaacaggcaggaggcggacacccattatgcgactgtgcaggacctaaaacgaaagtatt
 88    gcacaggcattgttaaacgcgcaggagggcgatgctcattatgcggctgtgcaggacctaaaacgaaagtatt
 89    gcacaggcacttttacatgtacagcagacatgtgcagatgctgctgacctgtgcgagttaaaacgaaagtacat
 90    gcgcaggctctgtttaaatgcacaacaagcggatgctgatgctgctatagtgcaggagttaaaacgaaagtacat
 91    gcacaagccttattaaataaacaacaagcacatgcagatcaggaggcagtacaggcactaaaacgaaagctatt
 92    ccacaggcattgttacatgcccaacagctgcaggcagatgtagaggcagtgcaacaattaaaacgaaagtatat
 93    -cgcttgcgttgttcgttcaacaaaatgcacaggatgacgctgcaacggtgcaggcactaaaacgaaagtatac
 94    gcacaggtactgtataatatgcaagaggcccaaagggatgcacaatcagtgcgtgccttaaaacgaaagtatgg
 95    -cgttagatttgttcgtgcaacaaaatgcacgggatgacgctgcaaccgtgcaggccctaaaacgaaagtatac
 96    -cgttagaactgtttgttcaacaaaatgcacaggatgacgctgcagcggtgcatgcactaaaacgaaagtatat
```

Techniques for nucleic acid manipulation useful for the practice of the present invention are described in a variety of references, including but not limited to, Molecular Cloning: A Laboratory Manual, 2nd ed., Vol. 1-3, eds. Sambrook et al. Cold Spring Harbor Laboratory Press (1989); and Current Protocols in Molecular Biology, eds. Ausubel et al., Greene Publishing and Wiley-Interscience: New York (1987) and periodic updates. Specific descriptions, while not intended to limit the scope of the present invention, provide guidance in practicing certain aspects of the present invention.

DNA is subject to degradation by DNases present in bodily fluids, such as urine. The present invention encompasses several methods for preventing or reducing the degradation of DNA while in urine so that sufficiently large sequences are available for detection by known methods of DNA detection such as those described below. In one embodiment, samples of urine are taken when the urine has been held in the bladder for less than 12 hours, in a specific embodiment the urine is held in the bladder for less than 5 hours, more preferable for less than 2 hours. Collecting and analyzing a urine sample before it has been held in the bladder for a long period of time reduces the exposure of DNA to the any DNase present in the urine.

In another embodiment of the present invention, after collection, the urine sample is treated using one or more methods of inhibiting DNase activity. Methods of inhibiting DNase activity include, but are not limited to, the use of ethylenediaminetetraacetic acid (EDTA), guanidine-HC1, GITC (Guanidine isothiocyanate), N-lauroylsarcosine, Na-dodecylsulphate (SDS), high salt concentration and heat inactivation of DNase.

In yet another embodiment, after collection, the urine sample is treated with an adsorbent that traps DNA, after which the adsorbent is removed from the sample, rinsed and treated to release the trapped DNA for detection and analysis. This method not only isolates DNA from the urine sample, but, when used with some adsorbents, including, but not limited to Hybond N membranes (Amersham Pharmacia Biotech Ltd., Piscataway, N.J.) protects the DNA from degradation by DNase activity.

In some cases, the amount of DNA in a urine sample is limited. Therefore, for certain applications, the present invention encompasses embodiments wherein sensitivity of detection is increased by any method(s) known in the art, including, without limitation, one or more of the following methods.

Where DNA is present in minute amounts in the urine, larger urine samples can be collected and thereafter concentrated by any means that does not effect the detection of DNA present in the sample. Some examples include, without limiting the breadth of the invention, reducing liquid present in the sample by butanol concentration or concentration using Sephadex G-25 (Pharmacia Biotech, Inc., Piscataway N.J.).

Nested PCR can be used to improve sensitivity by several orders of magnitude. Because of the vulnerability of nested PCR to inaccurate results due to DNA contamination, in one embodiment of the present invention, precautions are taken to avoid DNA contamination of the sample. For example, without limiting the present invention, one can treat PCR reagents with restriction endonuclease(s) that cleave within the target sequence, prior to adding them to the test DNA sample.

In one embodiment, the present invention encompasses substantially purifying or isolating nucleic acids from a sample prior to detection. Nucleic acid molecules can be isolated from urine using any of a number of procedures, which are well-known in the art. Any method for isolation that facilitates the detection of target nucleic acid is acceptable.

For example, DNA can be isolated by precipitation, as described by Ishizawa et al., Nucleic Acids Res. 19, 5972 (1991). Where a large volume sample contains a low concentration of DNA, as with urine, a preferred method of isolating DNA is encompassed. In this method, a sample is treated with an adsorbent that acts to concentrate the DNA. For example, a sample can be treated with a solid material that will adsorb DNA, such as, without limitation, DEAE Sephadex A-25 (Pharmacia Biotech, Inc., Piscataway N.J.), a DNA filter, and/or glass milk. Sample DNA is eluted from the adsorbent after other compositions are washed away.

In consideration of the sensitivity of various nucleic acid analyzing techniques, such as PCR, the present invention also encompasses methods of reducing the presence of contaminating nucleic acids in the urine sample. Contamination of urine samples by nucleic acid sequences that have not crossed the kidney barrier can be introduced by cells shedding from the urinary tract lining, by sexual intercourse, or during processing of the urine sample prior to detection of the DNA sequence of interest. Without intending to limit the present invention to any mechanism, it is believed that DNA passing the kidney barrier and appearing in urine is likely to have on average a shorter length than DNA introduced from contaminating sources because of the fragmentation that occurs in apoptotic cells and necrotic cells in the body, combined with the action of DNase in the blood and urine.

Filtration can be used to reduce the level of contaminating DNA in a urine sample prior to detection, by selecting for shorter sequences of DNA. In one embodiment of the present invention nucleic acids containing more than about 1000 base pairs, or 1000 nucleotides when denatured, are removed from the sample prior to detection. In a specific embodiment of the present invention, urine samples are filtered prior to amplification by PCR to remove substantially all DNA comprising greater than 300 base pairs, or 300 nucleotides when denatured. Without limiting the invention to a specific mechanism, it is proposed that such a filtration removes contaminating DNA from cells shed from the urethral/bladder wall or introduced into the urethra during sexual intercourse. The majority of DNA from such contaminating sources are likely to comprise more than 300 by nucleotides as the DNA is not for the most part a product of fragmentation of nucleic acids as a result of apoptotic cell death. Nucleic acid molecules can also be isolated by gel electrophoresis, whereby fragments of nucleic acid are separated according to molecular weight. The technique of restriction fragments length polymorphisms (RFLP), applies the methods of electrophoresis separation, followed by nucleic acid detection enabling comparison by molecular weight of fragments from two or more alleles of a specific gene sequence.

The above-mentioned methods of purification are meant to describe, but not limit, the methods suitable for use in the invention. The methods of isolating nucleic acids are within the ability of one skilled in the art and are not described in detail here.

The present invention further encompasses methods having the step of reducing DNA degradation in said urine sample, which in one embodiment encompasses treatment with a compound selected from the group comprising: ethylenediaminetetraacetic acid, guanidine-HC1, Guanidine isothiocyanate, N-lauroylsarcosine, and Na-dodecylsulphate. DNA degradation can further be reduced by taking a urine sample that has been held in the bladder less than 12 hours. In one embodiment, it is beneficial to substantially isolate said nucleic acid sequence prior to assaying the urine for the presence of HPV nucleic acid sequence, that has crossed the kidney barrier. In alternate embodiments, the nucleic acid sequence is substantially isolated by precipitation or by treatment with a solid adsorbent material. In another embodiment, the urine sample is filtered to remove contaminants, and, in a specific embodiment, the filtering removes DNA comprising more than about 1000 nucleotides. Preferably, the filtering removes DNA comprising more than about 300 nucleotides.

The terms "detect" and "analyze" in relation to a nucleic acid sequence, refer to the use of any method of observing, ascertaining or quantifying signals indicating the presence of the target nucleic acid sequence in a sample or the absolute or relative quantity of that target nucleic acid sequence in a sample. Methods can be combined with nucleic acid labeling methods to provide a signal by, for example: fluorescence, radioactivity, colorimetry, gravimetry, X-ray diffraction or adsorption, magnetism, enzymatic activity and the like. The signal can then be detected and/or quantified, by methods appropriate to the type of signal, to determine the presence or absence, of the specific DNA sequence of interest.

To "quantify" in relation to a nucleic acid sequence, refers to the use of any method to study the amount of a particular nucleic acid sequence, including, without limitation, methods to determine the number of copies of a nucleic acid sequence or to determine the change in quantity of copies of the nucleic acid sequence over time, or to determine the relative concentration of a sequence when compared to another sequence.

To assist in detection and analysis, specific DNA sequences can be "amplified" in a number of ways, including, but not limited to cycling probe reaction (Bekkaoui, F. et al, BioTechniques 20,240-248 (1996), polymerase chain reaction (PCR), nested PCR, PCR-SSCP (single strand conformation polymorphism), ligase chain reaction (LCR) (F. Barany Proc. Natl. Acad. Sci USA 88:189-93 (1991)), cloning, strand displacement amplification (SDA) (G. K. Terrance Walker et al., Nucleic Acids Res. 22:2670-77 (1994), and variations such as allele-specific amplification (ASA).

To facilitate understanding of the invention, a number of terms are defined below.

The term "gene" refers to a DNA sequence that comprises control and coding sequences necessary for the transcription of an RNA sequence. The term "genome" refers to the complete gene complement of an organism, contained in a set of chromosomes in eukaryotes.

A "wild-type" gene or gene sequence is that which is most frequently observed in a population and is thus arbitrarily designed the "normal" or "wild-type" form of the gene. In contrast, the term "modified", "mutant", "anomaly" or "altered" refers to a gene, sequence or gene product which displays modifications in sequence and or functional properties (i.e., altered characteristics) when compared to the wild-type gene, sequence or gene product. It is noted that naturally-occurring mutants can be isolated; these are identified by the fact that they have altered characteristics when compared to the wild-type gene or gene product. Without limiting the invention to the detection of any specific type of anomaly, mutations can take many forms, including addition, addition-deletion, deletion, frame-shift, missense, point, reading frame shift, reverse, transition and transversion mutations as well as microsatellite alterations.

The terms "oligonucleotide" and "polynucleotide" and "polymeric" nucleic acid are interchangeable and are defined as a molecule comprised of two or more deoxyribonucleotides or ribonucleotides, preferably more than three, and usually more than ten. The exact size will depend on many factors, which in turn depends on the ultimate function or use of the oligonucleotide. The oligonucleotide can be generated in any manner, including chemical synthesis, DNA replication, reverse transcription, or a combination thereof.

Because mononucleotides are reacted to make oligonucleotides in a manner such that the 5' phosphate of one mononucleotide pentose ring is attached to the 3' oxygen of its neighbor in one direction via a phosphodiester linkage, an end of an oligonucleotide is referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide, also can be said to have 5' and 3' ends.

When two different, non-overlapping oligonucleotides anneal to different regions of the same linear complementary nucleic acid sequence, and the 3' end of one oligonucleotide points towards the 5' end of the other, the former can be called the "upstream" oligonucleotide and the latter the "downstream" oligonucleotide.

The term "primer" refers to an oligonucleotide which is capable of acting as a point of initiation of synthesis when placed under conditions in which primer extension is initiated. An oligonucleotide "primer" can occur naturally, as in a purified restriction digest or be produced synthetically.

A primer is selected to be "substantially" complementary to a strand of specific sequence of the template. A primer must be sufficiently complementary to hybridize with a template strand for primer elongation to occur. A primer sequence need not reflect the exact sequence of the template. For example, a non-complementary nucleotide fragment can be attached to the 5' end of the primer, with the remainder of the primer sequence being substantially complementary to the strand. Non-complementary bases or longer sequences can be interspersed into the primer, provided that the primer sequence has sufficient complementarity with the sequence of the template to hybridize and thereby form a template primer complex for synthesis of the extension product of the primer.

A "target" nucleic acid is a nucleic acid sequence to be evaluated by hybridization, amplification or any other means of analyzing a nucleic acid sequence, including a combination of analysis methods.

"Hybridization" methods involve the annealing of a complementary sequence to the target nucleic acid (the sequence to be analyzed). The ability of two polymers of nucleic acid containing complementary sequences to find each other and anneal through base pairing interaction is a well-recognized phenomenon. The initial observations of the "hybridization" process by Marmur and Lane, Proc. Natl. Acad. Sci. USA 46:453 (1960) and Doty et al., Proc. Natl. Acad. Sci. USA 46:461 (1960) have been followed by the refinement of this process into an essential tool of modern biology. Hybridization encompasses, but is not limited to, slot, dot and blot hybridization techniques.

It is important for some diagnostic applications to determine whether the hybridization represents complete or partial complementarity. For example, where it is desired to detect simply the presence or absence of pathogen DNA (such as from a virus, bacterium, fungi, mycoplasma, protozoan) it is only important that the hybridization method ensures hybridization when the relevant sequence is present; conditions can be selected where both partially complementary probes and completely complementary probes will hybridize. Other diagnostic applications, however, could require that the hybridization method distinguish between partial and complete complementarity. It may be of interest to detect genetic polymorphisms.

Methods that allow for the same level of hybridization in the case of both partial as well as complete complementarity are typically unsuited for such applications; the probe will hybridize to both the normal and variant target sequence. The present invention contemplates that for some diagnostic purposes, hybridization be combined with other techniques (such as restriction enzyme analysis). Hybridization, regardless of the method used, requires some degree of complementarity between the sequence being analyzed (the target sequence) and the fragment of DNA used to perform the test (the probe). (Of course, one can obtain binding without any complementarity but this binding is nonspecific and to be avoided.)

The complement of a nucleic acid sequence as used herein refers to an oligonucleotide which, when aligned with the nucleic acid sequence such that the 5' end of one sequence is paired with the 3' end of the other, is in "antiparallel association." Specific bases not commonly found in natural nucleic acids can be included in the nucleic acids of the present invention and include, for example, inosine and 7-deazaguanine. Complementarity need not be perfect; stable duplexes can contain mismatched base pairs or unmatched bases. Those skilled in the art of nucleic acid technology can determine duplex stability empirically considering a number of variables including, for example, the length of the oligonucleotide, base composition and sequence of the oligonucleotide, ionic strength and incidence of mismatched base pairs.

As used herein, the term "Tm" is used in reference to the "melting temperature." The melting temperature is the temperature at which a population of double-stranded nucleic acid molecules becomes half dissociated into single strands. The equation for calculating the Tm of nucleic acids is well known in the art. As indicated by standard references, a simple estimate of the Tm value can be calculated by the equation: $Tm=81.5+0.41(\% G+C)$, when a nucleic acid is in aqueous solution at 1 M NaCl (see e.g., Anderson and Young, Quantitative Filter Hybridisation, in Nucleic Acid Hybridisation (1985). Other references include more sophisticated computations which take structural as well as sequence characteristics into account for the calculation of Tm.

The term "probe" as used herein refers to an oligonucleotide (i.e., a sequence of nucleotides), whether occurring naturally as in a purified restriction digest or produced synthetically, which forms a duplex structure or other complex with a sequence in another nucleic acid, due to complementarity or other means of reproducible attractive interaction, of at least one sequence in the probe with a sequence in the other nucleic acid. Probes are useful in the detection, identification and isolation of particular gene sequences. It is contemplated that any probe used in the present invention will be labeled with any "reporter molecule," so that it is detectable in any detection system, including, but not limited to, enzyme (e.g., ELISA, as well as enzyme-based histochemical assays), fluorescent, radioactive, and luminescent systems. It is further contemplated that the oligonucleotide of interest (i.e., to be detected) will be labeled with a reporter molecule. It is also contemplated that both the probe and oligonucleotide of interest will be labeled. It is not intended that the present invention be limited to any particular detection system or label.

The term "label" as used herein refers to any atom or molecule which can be used to provide a detectable (preferably quantifiable) signal, and which can be attached to a nucleic acid or protein. Labels provide signals detectable by any number of methods, including, but not limited to, fluorescence, radioactivity, colorimetry, gravimetry, X-ray diffraction or absorption, magnetism, and enzymatic activity.

The term "substantially single-stranded" when used in reference to a nucleic acid target means that the target molecule exists primarily as a single strand of nucleic acid in contrast to a double-stranded target which exists as two strands of nucleic acid which are held together by inter-strand base pairing interactions.

The term "sequence variation" as used herein refers to differences in nucleic acid sequence between two nucleic acid templates. For example, a wild-type structural gene and a mutant form of this wild-type structural gene can vary in sequence by the presence of single base substitutions and/or deletions or insertions of one or more nucleotides. These two forms of the structural gene are said to vary in sequence from one another. A second mutant form of the structural gene can exit. This second mutant form is said to vary in sequence from both the wild-type gene and the first mutant form of the gene.

The terms "structure probing signature," "hybridization signature" and "hybridization profile" are used interchangeably herein to indicate the measured level of complex formation between a target nucleic acid and a probe or set of probes, such measured levels being characteristic of the target nucleic acid when compared to levels of complex formation involving reference targets or probes.

"Oligonucleotide primers matching or complementary to a gene sequence" refers to oligonucleotide primers capable of facilitating the template-dependent synthesis of single or double-stranded nucleic acids. Oligonucleotide primers matching or complementary to a gene sequence can be used in PCRs, RT-PCRs and the like.

"Nucleic acid sequence" as used herein refers to an oligonucleotide, nucleotide or polynucleotide, and fragments or portions thereof, and to DNA or RNA of genomic or synthetic origin which can be single- or double-stranded, and represent the sense or antisense strand.

A "deletion" is defined as a change in either nucleotide or amino acid sequence in which one or more nucleotides or amino acid residues, respectively, are absent.

An "insertion" or "addition" is that change in a nucleotide or amino acid sequence which has resulted in the addition of one or more nucleotides or amino acid residues, respectively, as compared to, naturally occurring sequences.

A "substitution" results from the replacement of one or more nucleotides or amino acids by different nucleotides or amino acids, respectively.

A "modification" in a nucleic acid sequence refers to any change to a nucleic acid sequence, including, but not limited to a deletion, an addition, an addition-deletion, a substitution, an insertion, a reversion, a transversion, a point mutation, a microsatellite alteration, methylation or nucleotide adduct formation.

As used herein, the terms "purified", "decontaminated" and "sterilized" refer to the removal of contaminant(s) from a sample.

As used herein, the terms "substantially purified" and "substantially isolated" refer to nucleic acid sequences that are removed from their natural environment, isolated or separated, and are preferably 60% free, more preferably 75% free, and most preferably 90% free from other components with which they are naturally associated. An "isolated polynucleotide" is therefore a substantially purified polynucleotide. It is contemplated that to practice the methods of the present invention polynucleotides can be, but need not be substantially purified. A variety of methods for the detection of nucleic acid sequences in unpurified form are known in the art.

"Amplification" is defined as the production of additional copies of a nucleic acid sequence and is generally carried out using polymerase chain reaction or other technologies well known in the art (e.g., Dieffenbach and Dveksler, PCR Primer, a Laboratory Manual, Cold Spring Harbor Press, Plainview, N.Y. [1995]). As used herein, the term "polymerase chain reaction" ("PCR") refers to the method of K. B. Mullis (U.S. Pat. Nos. 4,683,195 and 4,683,202, hereby incorporated by reference), which describe a method for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified".

As used herein, the term "polymerase" refers to any enzyme suitable for use in the amplification of nucleic acids of interest. It is intended that the term encompass such DNA polymerases as Taq DNA polymerase obtained from Thermus aquaticus, although other polymerases, both thermostable and thermolabile are also encompassed by this definition. With PCR, it is possible to amplify a single copy of a specific target sequence in genomic DNA to a level that can be detected by several different methodologies (e.g., staining, hybridization with a labeled probe; incorporation of biotinylated primers followed by avidin-enzyme conjugate detection; incorporation of 32P-labeled deoxynucleotide triphosphates, such as dCTP or dATP, into the amplified segment). In addition to genomic DNA, any oligonucleotide sequence can be amplified with the appropriate set of primer molecules. In particular, the amplified segments created by the PCR process itself are, themselves, efficient templates for subsequent PCR amplifications. Amplified target sequences can be used to obtain segments of DNA (e.g., genes) for insertion into recombinant vectors.

As used herein, the terms "PCR product" and "amplification product" refer to the resultant mixture of compounds after two or more cycles of the PCR steps of denaturation, annealing and extension are complete. These terms encompass the case where there has been amplification of one or more segments of one or more target sequences.

As used herein, the terms "restriction endonucleases" and "restriction enzymes" refer to bacterial enzymes, each of which cut double-stranded DNA at or near a specific nucleotide sequence.

As used herein, the terms "complementary" or "complementarity" are used in reference to polynucleotides (i.e., a sequence of nucleotides) related by the base-pairing rules. For example, for the sequence "A-G-T," is complementary to the sequence "T-C-A." Complementarity can be "partial," in which only some of the nucleic acids' bases are matched according to the base pairing rules. Or, there can be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

The term "homology" refers to a degree of complementarity. There can be partial homology or complete homology (i.e., identity). A partially complementary sequence is one that at least partially inhibits a completely complementary sequence from hybridizing to a target nucleic acid is referred to using the functional term "substantially homologous." The inhibition of hybridization of the completely complementary sequence to the target sequence can be examined using a hybridization assay (Southern or Northern blot, solution hybridization and the like) under conditions of low stringency. A substantially homologous sequence or probe will compete for and inhibit the binding (i.e., the hybridization) of a completely homologous to a target under conditions of low stringency. This is not to say that conditions of low stringency are such that are non-specific binding is permitted; low stringency conditions require that the binding of two sequences to one another be a specific (i.e., selective) interaction. The absence of non-specific binding can be tested by the use of a second target which lacks even a partial degree of complementarity (e.g., less than about 30% identity); in the absence of non-specific binding the probe will not hybridize to the second non-complementary target.

Numerous equivalent conditions can be employed to comprise either low or high stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution can be varied to generate conditions of either low or high stringency hybridization different from, but equivalent to, the above listed conditions. The term "hybridization" as used herein includes "any process by which a strand of nucleic acid joins with a complementary strand through base pairing" (Coombs, Dictionary of Biotechnology, Stockton Press, New York N.Y. [1994].

"Stringency" typically occurs in a range from about Tm-5° C. (5° C. below the Tm of the probe) to about 20° C. to 25° C. below Tm. As will be understood by those of skill in the art, a stringent hybridization can be used to identify or detect identical polynucleotide sequences or to identify or detect similar or related polynucleotide sequences.

As used herein the term "hybridization complex" refers to a complex formed between two nucleic acid sequences by virtue of the formation of hydrogen bonds between complementary G and C bases and between complementary A and T bases; these hydrogen bonds can be further stabilized by base stacking interactions. The two complementary nucleic acid sequences hydrogen bond in an antiparallel configuration. A hybridization complex can be formed in solution (e.g., C0t or R0t analysis) or between one nucleic acid sequence present in solution and another nucleic acid sequence immobilized to a solid support (e.g., a nylon membrane or a nitrocellulose filter as employed in Southern and Northern blotting, dot blotting or a glass slide as employed in situ hybridization, including FISH [fluorescent in situ hybridization]).

As used herein, the term "antisense" is used in reference to RNA sequences which are complementary to a specific RNA (e.g., mRNA) or DNA sequence. Antisense RNA can be produced by any method, including synthesis by splicing the gene(s) of interest in a reverse orientation to a viral promoter which permits the synthesis of a coding strand. Once introduced into a cell, this transcribed strand combines with natural mRNA produced by the cell to form duplexes. These duplexes then block either further transcription of the mRNA or its translation. In this manner, mutant phenotypes can be generated. The term "antisense strand" is used in reference to a nucleic acid strand that is complementary to the "sense" strand. The designation (−) (i.e., "negative") is sometimes used in reference to the antisense strand, with the designation (+) sometimes used in reference to the sense (i.e., "positive") strand.

The term "sample" as used herein is used in its broadest sense. A biological sample suspected of containing nucleic acid can comprise, but is not limited to, genomic DNA (in solution or bound to a solid support such as for Southern blot analysis), cDNA (in solution or bound to a solid support), and the like.

The term "urinary tract" as used herein refers to the organs and ducts which participate in the secretion and elimination of urine from the body.

The terms "transrenal DNA" and "transrenal nucleic acid" as used herein refer to nucleic acids that have crossed the kidney barrier. Transrenal DNA as used herein differs from miRNA. Specifically, transrenal DNA comprises randomness in the 3' and 5' ends, which is not present in miRNA.

The invention is further described below, by way of the following examples. The examples also illustrate useful methodology for practicing the invention. These examples do not limit the claimed invention.

EXAMPLES

Example 1

Purification of Total Urine Nucleic Acids

Urine Preparation:

Urine specimens were collected in containers, which are capable of holding a volume of at least 100 ml.

Prior to urination, the collection cups were prefilled with sufficient EDTA to achieve a final concentration of 50 mM when containers are full (e.g. 10 ml of 0.5M EDTA=50 mM when diluted up to 100 ml with urine). Urine specimens were stored at −80° C. Frozen urine was thawed at room temperature.

Q-Sepharose Step

For a standard batch size of 10 ml urine (prior to dilution) 1.0 ml of Q-Sepharose slurry (Q-Sepharose stock: 25 ml size from GE Healthcare; 250 µL resin) was used.

Binding of urinary NA to Q-Sepharose was performed for 30 min at room temperature (20-25° C.) with rotation in a 50 mL tube. The resin was collected by centrifugation at room temperature (800-1000×g for 5 min) and transferred into an empty disposable column The resin was washed twice with at least 1 mL of 0.3 M LiCl/10 mM NaOAc (pH 5). NA was eluted with 750 µL of 2 M LiCl/10 mM NaOAc.

Silica Purification:

DNA Eluted from Q-sepharose NA in 750 µl buffer was supplemented with 2.25 mL of 95% EtOH and applied to a silica column (Qiagen or equivalent). If column extension was used one load took the whole mixture, otherwise several loads were performed. The column was centrifuged for 1 minute in a table top microcentrifuge (Eppendorf). Alternatively, a vacuum manifold was used.

Silica column was washed with 500 µL of 2 M LiCl in 70% EtOH by centrifugation at 5000 rpm for 1 min. Followed with two washes with 75 mM KOAc pH 5.0, 80% EtOH. NA was eluted with 100 µL of 1 mM Tris-HCl (pH 8.0)/0.025 mM EDTA (pH 8.0).

Routinely 5 µl was used for 25 µl PCR reaction.

Example 2

Use of specific PCR primers mapped to the E1 gene for amplification of HPV Individual Genotypes Primers were tested, which were designed to be specific to a single type of high risk HPV and mapped in the disclosed fragment of E1 gene. These primers are listed in Table 3. In the PCR, each forward primer was paired with a corresponding reverse primer at a 500 nM concentration. Per PCR, the final concentration of $MgCl_2$ was 2 mM and the final concentration of JumpStart Taq DNA polymerase was 1.25 U/reaction. Individual oligonucleotides corresponding to high risk HPV types were used as templates at 1000 copies per reaction (see, Table 2). The predicted size of the PCR product was 47 base pairs (bp).

Figure 2:
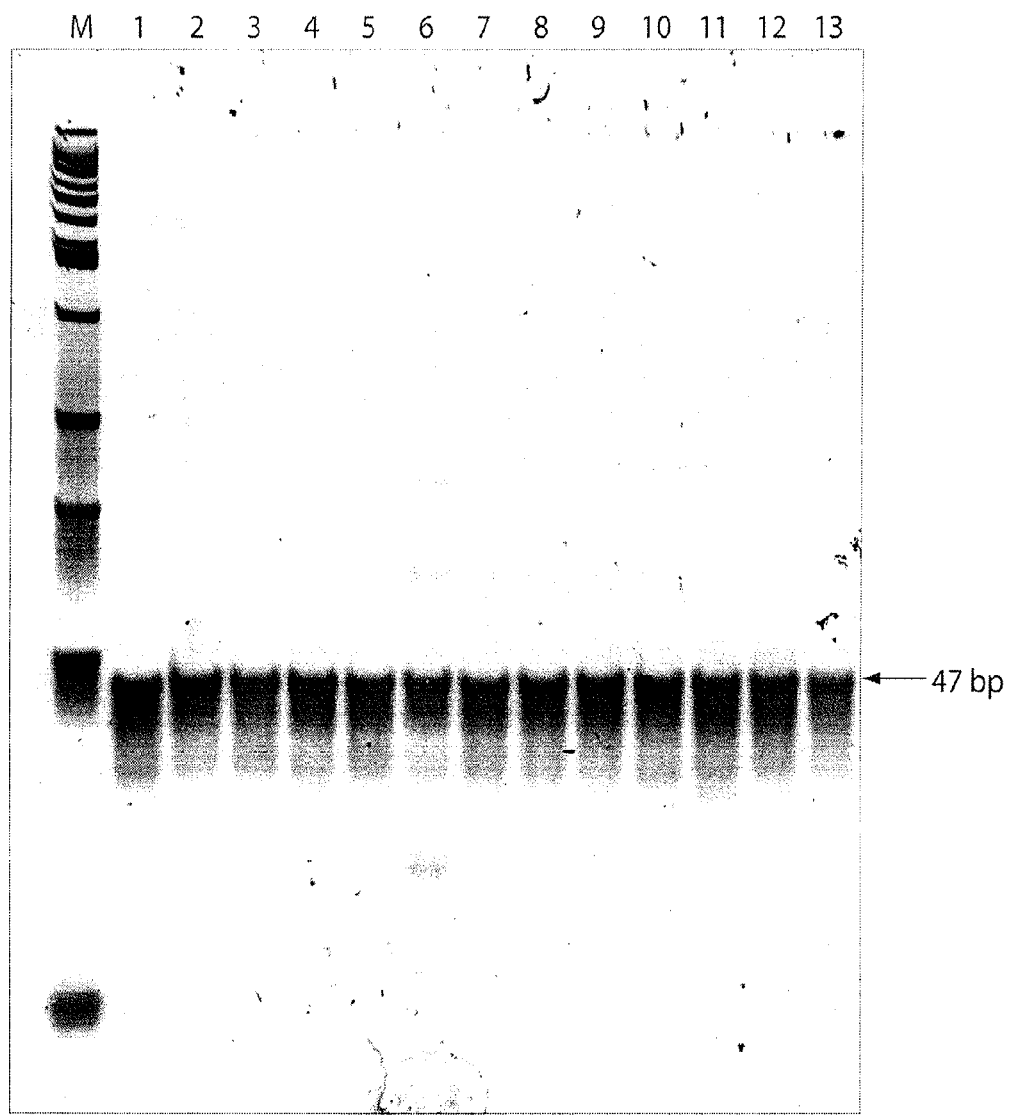
FIG. 2 is a photograph of a gel electrophoresis analysis depicting PCR products of individual HPV genotypes, which were amplified using primers mapped to the E1 gene of HPV.

Amplification was performed according to the following program:
1 cycle
94° C.—2 min (Enzyme activation)
5 cycles
94° C.—30 sec
65° C.—2 min
5 cycle
94° C.—30 sec
60° C.—1 min
35 cycle
94° C.—30 sec
55° C.—1 min
1 cycle
72° C.—5min
4° C.—forever Products of the reaction are presented in FIG. 2, wherein lane numbers from 1 to 13 correspond to the following high risk HPV genotypes: 16; 18; 31; 33; 35; 39; 45; 51; 52; 56; 58; 59; 68, respectively. The molecular weight marker ("M") is a 25 by ladder.

TABLE 2

Individual oligonucleotides corresponding to high risk HPV types

| SEQ ID | HPV | Nucleotide Sequence |
|---|---|---|
| 1 | 16 | CAGTGATACAGGTGAAGATTTGGTAGATTTTATAGTAAATGATAATGATTATTTA ACACAGGCAGAAACAGAGACAGCACATGCGTTGTTTACTGCACAGGAAGCAAAAC AACATAGAGATGCAGTACAGGTTCTAAAACGAAAGTATT |

TABLE 2-continued

Individual oligonucleotides corresponding to high risk HPV types

| SEQ ID | HPV | Nucleotide Sequence |
|---|---|---|
| 2 | 18 | AACAGACACAGGGTCGGATATGGTAGATTTTATTGATACACAAGGAACATTTTGT<br>GAACAGGCAGAGCTAGAGACAGCACAGGCATTGTTCCATGCGCAGGAGGTCCACA<br>ATGATGCACAAGTGTTGCATGTTTTAAAACGAAAGTTTG |
| 3 | 31 | TAGTGATACTGGGGAGGTATATGGTTGACTTTATTGACAATTGTAATGTATACAAC<br>AATCAGGCAGAAGCAGAGACAGCACAGGCATTGTTTCATGCACAGGAAGCGGAGG<br>AACATGCAGAGGCTGTGCAGGTTCTAAAACGAAAGTATG |
| 4 | 33 | AGATGACAGTGGCACGGATTTACTAGAGTTTATAGATGATTCTATGGAAAATAGT<br>ATACAGGCAGACACAGAGGCAGCCCGGGCATTGTTTAATATACAGGAAGGGGAGG<br>ATGATTTAAATGCTGTGTGTGCACTAAAACGAAAGTTTG |
| 5 | 35 | CTGTGACAGGGGGGAGGATATGGTGGACTTTATAAATGATACAGATATATTAAAC<br>ATACAGGCAGAAACAGAGACAGCACAAGCATTATTTCATGCACAGGAGGAGCAAA<br>CACACAAAGAGGCTGTACAGGTCCTAAAACGAAAGTATG |
| 6 | 39 | AACAGATACAGGTTCAGACCTGGCAGACTTTATTGATGATTCCACAGATATTTGT<br>GTACAGGCAGAGCGTGAGACAGCACAGGTACTTTTACATATGCAAGAGGCCCAAA<br>GGGATGCACAAGCAGTGCGTGCCTTAAAACGAAAGTATA |
| 7 | 45 | AACAGATACAGGGTCGGATATGGTAGATTTTATTGACACACAATTATCCATTTGT<br>GAACAGGCAGAGCAAGAGACAGCACAGGCATTGTTCCATGCGCAGGAAGTTCAGA<br>ATGATGCACAGGTGTTGCATCTTTTAAAACGAAAGTTTG |
| 8 | 51 | AGATGATACAGGATCTGATTTAATAAACTTTATAGATAGTGAAACTAGTATTTGC<br>AGTCAGGCGGAACAGGAGACAGCACGGGCGTTGTTTCAGGCCCAAGAATTACAGG<br>CAAACAAAGAGGCTGTGCATCAGTTAAAACGAAAGTTTC |
| 9 | 52 | ATATGATAGTGGAACAGATCTAATAGATTTTATAGATGATTCAAATATAAATAAT<br>GAACAGGCAGAACATGAGGCAGCCCGGGCATTGTTTAATGCACAGGAAGGGGAGG<br>ATGATTTACATGCTGTGTCTGCAGTAAAACGAAAGTTTA |
| 10 | 56 | GGATGAAATAGATACAGATTTAGATGGATTTATAGACGATTCATATATACAAAAT<br>ATACAGGCAGACGCAGAAACAGTCAACAATTGTTGCAAGTACAAACAGCACATGC<br>AGATAAACAGACGTTGCAAAAACTAAAACGAAAGTATA |
| 11 | 58 | AGACGATAGTGGTACAGATTTAATAGAGTTTATAGATGATTCAGTACAAAGTACT<br>ACACAGGCAGAAGCAGAGGCAGCCCGAGCGTTGTTTAATGTACAGGAAGGGGTGG<br>ACGATATAAATGCTGTGTGTGCACTAAAACGAAAGTTTG |
| 12 | 59 | AACAGATACAGGTTCAGACTTGGTAGATTTTATTGATGATACCACAACAATTTGT<br>GTACAGGCAGAGCGCGAGACAGCACAGGCCTTGTTTAATGTGCAGGAAGCCCAAA<br>GGGATGCACGGGAAATGCATGTTTTAAAACGAAAGTTTG |
| 13 | 68 | AAATGATACAGGGTCTGATATAATAGACTTTATAGATACAAATAACAGTATTTGC<br>AGTCAGGCGGAACAAGAGACAGCACGGGCGTTGTTTCAGGTCCAAGAAACACAGG<br>CACACAAAGAGGCTGCACAGCATCTAAAACGAAAGTTTT |
| 14 | 6 | GGTGGAGGACAGTGGGTATGACATGGTGGACTTTATTGATGACAGCAATATTACA<br>CACAATTCACTGGAAGCACAGGCATTGTTTAACAGGCAGGAGGCGGACACCCATT<br>ATGCGACTGTGCAGGACCTAAAACGAAAGTAT |
| 15 | 11 | GGTGGAGGACAGTGGGTATGACATGGTGGACTTTATTGATGACAGGCATATTACA<br>CAAAATTCTGTGGAAGCACAGGCATTGTTTAATAGGCAGGAGGCGGATGCTCATT<br>ATGCGACTGTGCAGGACCTAAAACGAAAGTAT |

TABLE 3

| SEQ ID | HPV | Primer Type | Sequence |
|---|---|---|---|
| 16 | 16 | Forward | CAGGCAGAAACAGAGACAG |
| 17 | 18 | Forward | CAGGCAGAGCTAGAGACAG |
| 18 | 31 | Forward | CAGGCAGAAGCAGAGACAG |
| 19 | 33 | Forward | CAGGCAGACACAGAGGCAG |
| 20 | 39 | Forward | CAGGCAGAGCGTGAGACAG |
| 21 | 45 | Forward | CAGGCAGAGCAAGAGACAG |
| 22 | 51 | Forward | CAGGCGGAACAGGAGACAG |
| 23 | 52 | Forward | CAGGCAGAACATGAGGCAG |
| 24 | 56 | Forward | CAGGCAGACGCAGAAACAG |
| 25 | 58 | Forward | CAGGCAGAAGCAGAGGCAG |
| 26 | 59 | Forward | CAGGCAGAGCGCGAGACAG |
| 27 | 68 | Forward | CAGGCGGAACAAGAGACAG |

TABLE 3-continued

| SEQ ID | HPV | Primer Type | Sequence |
|---|---|---|---|
| 28 | 16 | Reverse | TGCTTCCTGTGCAGTAAACAACG |
| 29 | 18 | Reverse | GACCTCCTGCGCATGGAACAATG |
| 30 | 31 | Reverse | CGCTTCCTGTGCATGAAACAATG |
| 31 | 33 | Reverse | CCCTTCCTGTATATTAAACAATG |
| 32 | 35 | Reverse | CTCCTCCTGTGCATGAAATAATG |
| 33 | 39 | Reverse | GGCCTCTTGCATATGTAAAGTAC |
| 34 | 45 | Reverse | AACTTCCTGCGCATGGAACAATG |
| 35 | 51 | Reverse | TAATTCTTGGGCCTGAAACAACG |
| 36 | 52 | Reverse | CCCTTCCTGTGCATTAAACAATG |
| 37 | 56 | Reverse | TGCTGTTTGTACTTGCAACAATTG |
| 38 | 58 | Reverse | CCCTTCCTGTACATTAAACAACG |
| 39 | 59 | Reverse | GGCTTCCTGCACATTAAACAAGG |
| 40 | 68 | Reverse | TGTTTCTTGGACCTGAAACAACG |

Example 3

Use of Single Pair of PCR Primers for Detection of all 13 High Risk HPV Genotypes The purpose of this experiment was to use a single pair of primers mapped in the fragment of interest of the HPV E1 gene for specific detection of all or most of the 13 high-risk HPV strain that do not react with low risk counterparts. SEQ ID 41: 5'-CAGGCAGAATTAGAGRCAGC-3' was used as the forward primer and SEQ ID 42: 5'-tccacca-caWACTTTCGTTTTA-3' was used as the reverse primer. Lowercase nucleotides in the reverse primer are the randomly selected tail to adjust the melting temperature (Tm) of the primer.

Expected size of the specific product was 97 bp. In the PCR, the forward primer was paired with the reverse primer at a concentration of 800 nM. In this reaction, the final concentration of $MgCl_2$ was 3 mM and the final concentration of the JumpStart Taq DNA polymerase was 1.25 U/reaction. Individual oligonucleotides corresponding to high and low risk HPV types were used as templates at 1000 copies per reaction (see, Table 2).

Figure 3:
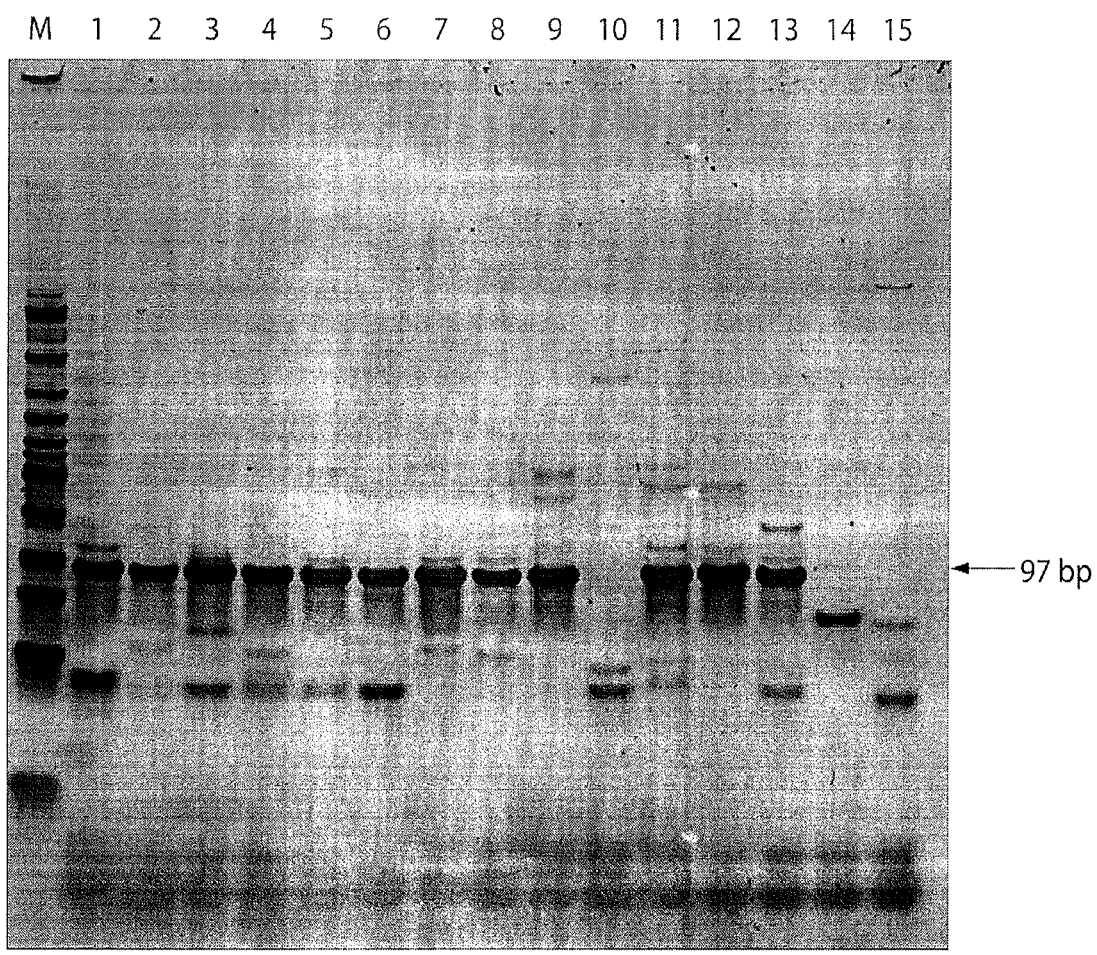
FIG. 3 is a photograph of a gel electrophoresis analysis depicting PCR products of individual HPV genotypes, which were amplified using a single primer pair, SEQ ID: 41 and SEQ ID: 42, mapped to the E1 gene of HPV.

Amplification was performed according to the following program:
1 cycle
94° C.—2 min (Enzyme activation)
40 cycles
94° C.—30 sec
50° C.—30 sec
72° C.—30 sec
1 cycle
72° C.—5min
4° C.—forever Products of the reaction are presented in FIG. 3, wherein lane numbers from 1 to 13 correspond to the following high risk HPV genotypes: 16; 18; 31; 33; 35; 39; 45; 51; 52; 56; 58; 59; 68, respectively, and lanes 14 and 15 correspond to low risk genotypes 6 and 11, respectively. The molecular weight marker ("M") is a 25 by ladder.

Example 4

Use of Single Pair of PCR Primers to Analyze Urine Samples from Patients with Cervical Cancer A single pair of primers that mapped in the fragment of interest of HPV E1 gene were used for specific detection of DNA of high risk HPV genotypes. Specifically, SEQ ID 41: 5'-CAGGCAGAATTAGAGRCAGC-3' was used as the forward primer and SEQ ID 42: 5'-tccacca-caWACTTTCGTTTTA-3' was used as the reverse primer. Lowercase nucleotides in the reverse primer are the randomly selected tail used to adjust the Tm of the primer. In the PCR, the forward primer was paired with the reverse primer at a concentration of 800 nM. In this reaction, final concentration of $MgCl_2$ was 3 mM and the final concentration of the JumpStart Taq DNA polymerase was 1.25 U/reaction.

DNA from Urine Samples were Extracted According to the Protocol Described in Example
1. Patients were asked to donate two urine samples: a first sample that was self-collected in the morning and a second sample that was collected at doctor's office later the same day (within a 24 hour period). Cervical samples were taken for the Digene tests. DNA from 10 ml of urine was extracted in 100 μl of elution buffer, of which 5 μl was used for PCR.

Figure 4:
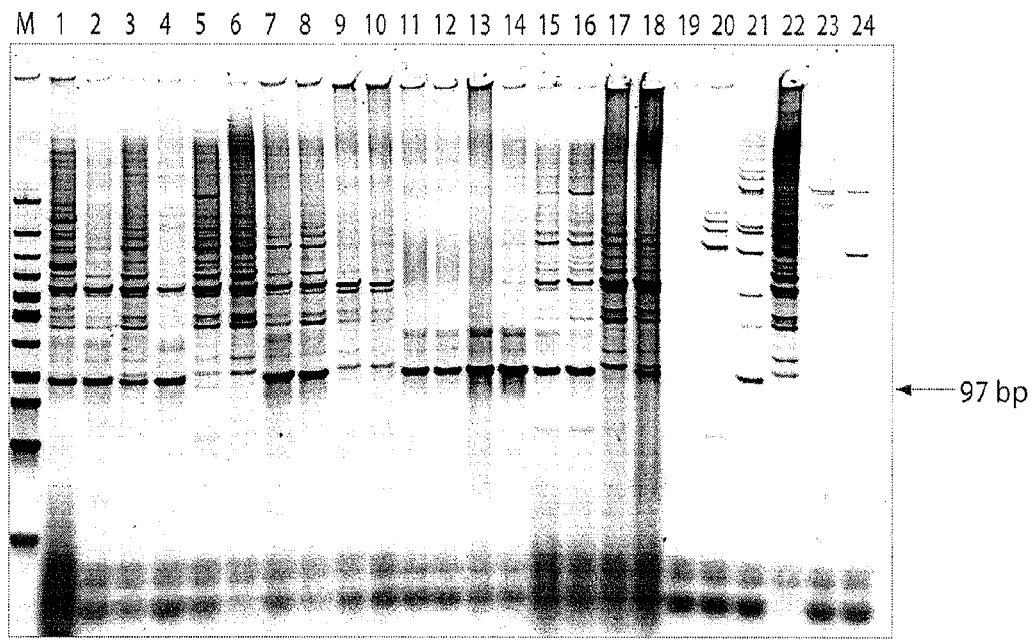
FIG. 4 is a photograph of a gel electrophoresis analysis depicting the PCR products of an HPV PCR test conducted on urine DNA collected from patients with cervical cancer, which was amplified using a single pair of primers SEQ ID: 41 and SEQ ID: 42, mapped to the E1 gene of HPV.

Amplification was performed according to the following program:
1 cycle
94° C.—2 min (Enzyme activation)
40 cycles
94° C.—30 sec
50° C.—30 sec
72° C.—30 sec
1 cycle
72° C.—5min
4° C.—forever Products of the reaction are presented in FIG. 4, wherein lane numbers from 1 to 18 represent urine samples of patients with cancer of the cervix. Odd lane numbers represent self-collected morning urine samples, whereas even lane numbers represent urine samples donated by the patients at the doctor's office later the same day. Specifically, lane 19 contained a urine sample from a healthy volunteer. Lane 20 contained water as a control for urine DNA purification. Lane 21 contained HPV 16 genomic DNA as a positive control. Lane 22 contained human genomic DNA (20,000 genome equivalent). Lane 23 contained an equivocal mix of low risk HPV 6 and 11 templates. And Lane 24 was a reaction control that contained no oligonucleotide or DNA template.

Example 5

Use of all HPV High Risk Specific PCR Primer Pairs in a Single Tube PCR for Detection of the Virus Oligonucleotide templates representing high risk genotypes (see, Table 2) were amplified by PCR with the mixture of all high risk specific primer pairs. In each reaction, a total of 25 PCR primers were included (see, Table 4). In the PCR, the forward primers, each used at a concentration of 200 nM, were each were combined with reverse primers, each used at a concentration of 300 nM. In this reaction, the final concentration of $MgCl_2$ was 2 mM and the final concentration of AmpliTaq DNA polymerase was 1.25 U/reaction. Individual oligonucleotides corresponding to high and low risk HPV types were used as templates at 1000 copies per reaction (Table 3).

Amplification was performed according to the following program:

1 cycle

94° C.—10 min (Enzyme activation)

40 cycles

94° C.—30 sec

60° C.—30 sec

72° C.—30 sec 1 cycle

72° C.—2min

4° C.—forever

Figure 5:
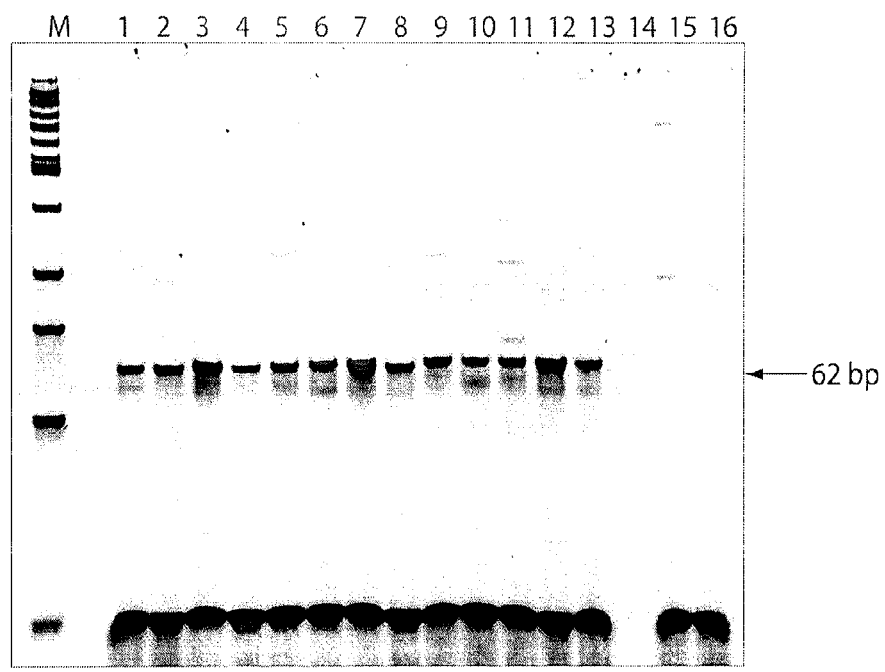
FIG. 5 is a photograph of a gel electrophoresis analysis depicting the PCR products of individual HPV genotypes, which were amplified using all high risk specific primers, mapped to the E1 gene of HPV (see, Table 4).

Expected size of the product was 62 bp. The footprint of the target was 51 bp. Results are depicted in FIG. 5, wherein lane numbers from 1 to 13 correspond to the following high risk HPV genotypes: 16; 18; 31; 33; 35; 39; 45; 51; 52; 56; 58; 59; 68, respectively, and lanes 15 and 16 correspond to low risk genotypes 6 and 11, respectively. The molecular weight marker ("M") is a 25 by ladder.

TABLE 4

| SEQ ID | HPV | Primer Type | Sequence |
|---|---|---|---|
| 43 | 16 | Forward | caactccatctACACAGGCAGAAACAGAGACAG |
| 44 | 18 | Forward | caactccatctGAACAGGCAGAGCTAGAGACAG |
| 45 | 31 | Forward | caactccatctAATCAGGCAGAAGCAGAGACAG |
| 46 | 33 | Forward | caactccatctATACAGGCAGACACAGAGGCAG |
| 47 | 35 | Forward | caactccatctATACAGGCAGAAACAGAGACAG |
| 48 | 39 | Forward | caactccatctGTACAGGCAGAGCGTGAGACAG |
| 49 | 45 | Forward | caactccatctGAACAGGCAGAGCAAGAGACAG |
| 50 | 52 | Forward | caactccatctGAACAGGCAGAACATGAGGCAG |
| 51 | 56 | Forward | caactccatctATACAGGCAGACGCAGAAACAG |
| 52 | 58 | Forward | caactccatctACACAGGCAGAAGCAGAGGCAG |
| 53 | 59 | Forward | caactccatctGTACAGGCAGAGCGCGAGACAG |
| 54 | 68 | Forward | caactccatctAGTCAGGCGGAACAAGAGACAG |
| 55 | 16 | Reverse | TGCTTCCTGTGCAGTAAACAACGCATG |
| 56 | 18 | Reverse | GACCTCCTGCGCATGGAACAATGC |
| 30 | 31 | Reverse | CGCTTCCTGTGCATGAAACAATG |
| 57 | 33 | Reverse | CCCTTCCTGTATATTAAACAATGCC |
| 58 | 35 | Reverse | CTCCTCCTGTGCATGAAATAATGCTTG |
| 33 | 39 | Reverse | GGCCTCTTGCATATGTAAAAGTAC |
| 34 | 45 | Reverse | AACTTCCTGCGCATGGAACAATG |
| 35 | 51 | Reverse | TAATTCTTGGGCCTGAAACAACG |
| 36 | 52 | Reverse | CCCTTCCTGTGCATTAAACAATG |
| 59 | 56 | Reverse | GTGCTGTTTGTACTTGCAACAATTG |
| 38 | 58 | Reverse | CCCTTCCTGTACATTAAACAACG |

TABLE 4-continued

| SEQ ID | HPV | Primer Type | Sequence |
|---|---|---|---|
| 39 | 59 | Reverse | GGCTTCCTGCACATTAAACAAGG |
| 40 | 68 | Reverse | TGTTTCTTGGACCTGAAACAACG |

Example 6

Use of all HPV High Risk Specific PCR Primer Pairs in a Single Tube PCR for Detection of the Virus Urine samples from patients with cervical cancer were tested using a mixture of all high risk specific primer pairs. Therefore, the PCR contained a total of 25 PCR primers in each reaction (see, Table 4). In the PCR, the forward primers, each used at a concentration of 200 nM, were combined with reverse primers, each used at a concentration of 300 nM. In this reaction, the final concentration of $MgCl_2$ was 2 mM and the final concentration of AmpliTaq DNA polymerase was 1.25 U/reaction. DNA from urine samples were extracted according to the protocol described in the Example 1. Urine samples collected at the visit to doctors office were used (see Example 5). DNA from 10 ml of urine was extracted in 100 µl of elution buffer, of which 5 µl was used for PCR.

Amplification was performed according to the following program:

1 cycle

94° C. —10 min (Enzyme activation)

40 cycles

94° C.—30 sec

60° C.—30 sec

72° C.—30 sec 1 cycle

72° C.—2min

4° C.—forever

Figure 6:
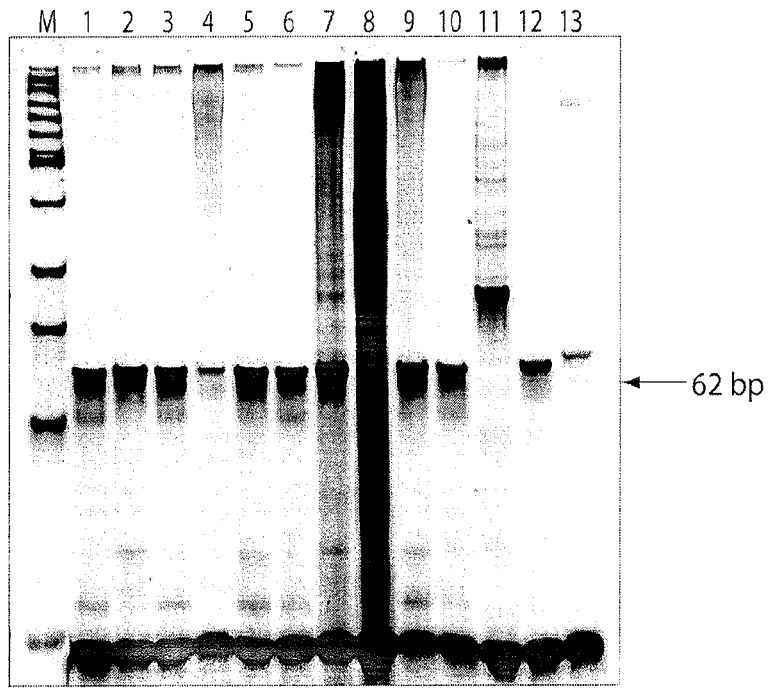
FIG. 6 is a photograph of a gel electrophoresis analysis depicting the PCR products of an HPV PCR test conducted on urine DNA collected from patients with cervical cancer, which was amplified using the mixture of all high risk specific primers in a single tube PCR reaction. The primers mapped to the E1 gene of HPV.

Expected size of the product was 62 bp. Results are depicted in FIG. 6, wherein lane numbers from 1 to 10 urine of patients with cancer of cervix. Specifically, Lane 11 contained human genomic DNA (20,000 genome equivalent). Lane 12 contained HPV 18 genomic DNA as a positive control. Lane 13 represented a reaction control that contained no oligonucleotide or DNA template.

Example 7

Use Of Subset of HPV High Risk Specific Primers in a Single Tube PCR for Detection of the Virus Oligonucleotides representing high risk HPV genotypes (Table 3) were amplified by PCR using a subset of high risk HP, the forward primers, each used at a concentration of 200 nM, were each were combined with a reverse primer, used at a concentration of 300 nM. In this reaction a total of 20 primers were used (Table 5) In this reaction, the final concentration of $MgCl_2$ was 2 mM and the final concentration of AmpliTaq DNA polymerase was 1.25 U/reaction. Individual oligonucleotides corresponding to high and low risk HPV types were used at 1000 copies per reaction (Table 2).

Figure 7:
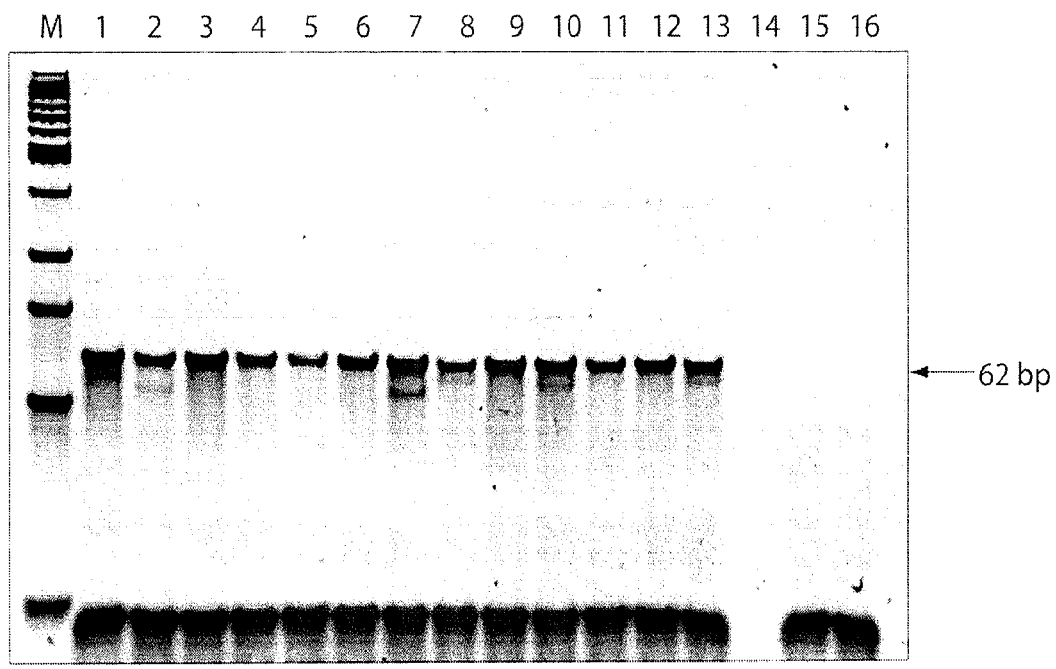
FIG. 7 is a photograph of a gel electrophoresis analysis depicting the PCR products of individual HPV genotypes using a subset of high risk specific primers, mapped to the E1 gene of HPV (see, Table 5).

Amplification was performed according to the following program:
1 cycle
94° C.—10 min (Enzyme activation)
40 cycles
94° C.—30 sec
62° C.—30 sec
1 cycle
72° C.—2min
4° C.—forever Expected size of the product was 62 bp. The footprint of the target was 51 bp. Results are depicted in FIG. 7, wherein lane numbers from 1 to 13 correspond to the following high risk HPV genotypes: 16; 18; 31; 33; 35; 39; 45; 51; 52; 56; 58; 59; 68, respectively, and lanes 15 and 16 correspond to low risk genotypes 6 and 11, respectively. The molecular weight marker ("M") is a 25 by ladder.

TABLE 5

| SEQ ID | HPV | Primer Type | Sequence |
|---|---|---|---|
| 43 | 16 | Forward | caactccatctACACAGGCAGAAACAGAGACAG |
| 44 | 18 | Forward | caactccatctGAACAGGCAGAGCTAGAGACAG |
| 46 | 33 | Forward | caactccatctATACAGGCAGACACAGAGGCAG |
| 48 | 39 | Forward | caactccatctGTACAGGCAGAGCGTGAGACAG |
| 49 | 45 | Forward | caactccatctGAACAGGCAGAGCAAGAGACAG |
| 50 | 52 | Forward | caactccatctGAACAGGCAGAACATGAGGCAG |
| 51 | 56 | Forward | caactccatctATACAGGCAGACGCAGAAACAG |
| 52 | 58 | Forward | caactccatctACACAGGCAGAAGCAGAGGCAG |
| 54 | 68 | Forward | caactccatctAGTCAGGCGGAACAAGAGACAG |
| 55 | 16 | Reverse | TGCTTCCTGTGCAGTAAACAACGCATG |
| 56 | 18 | Reverse | GACCTCCTGCGCATGGAACAATGC |
| 30 | 31 | Reverse | CGCTTCCTGTGCATGAAACAATG |
| 57 | 33 | Reverse | CCCTTCCTGTATATTAAACAATGCC |
| 58 | 35 | Reverse | CTCCTCCTGTGCATGAAATAATGCTTG |
| 33 | 39 | Reverse | GGCCTCTTGCATATGTAAAAGTAC |
| 35 | 51 | Reverse | TAATTCTTGGGCCTGAAACAACG |
| 36 | 52 | Reverse | CCCTTCCTGTGCATTAAACAATG |
| 59 | 56 | Reverse | GTGCTGTTTGTACTTGCAACAATTG |
| 38 | 58 | Reverse | CCCTTCCTGTACATTAAACAACG |
| 39 | 59 | Reverse | GGCTTCCTGCACATTAAACAAGG |

Example 8

An Improved Molecular Screening Test for The Detection of High Risk HPV in Urine of High and Low Risk Populations in India The Xenomics Transrenal DNA (Tr-DNA) technology is based on DNA fragments from cells dying throughout the body. This DNA appears in the bloodstream and is excreted into the urine. Analysis of urine samples was applied to detection of Y chromosome-specific DNA sequences from women with male fetuses, mutant K-ras in colorectal cancer patients, and *Mycobacterium tuberculosis* in patients with pulmonary tuberculosis.

The HPV DNA test used in this study involves isolation of DNA from urine and specific amplification of the HPV E1 region to detect the presence of high risk HPV types that have been associated with cervical cancer. These high-risk types include HPV 16, 18, 31, 33, 35, 39, 45, 51, 52, 56, 58, 59 and 68. DNA is amplified by the Polymerase Chain Reaction (PCR) using a FAM-labeled forward primer and an unlabelled reverse primer. These primers generate a 93-96 base pair (bp) amplicon as determined by capillary electrophoresis (CE). No cross-reactivity was observed with the low risk HPV types 6 and 11. Data obtained demonstrated that sensitivity and specificity of this test were equivalent to or better than those of a current assay in clinical use based on cervical scraping.

Methods

Sample Collection

Samples were collected from high and low risk populations in India including those from staged cancer patients by Simbiosys Biowares Inc. and Metropolis Inc. High Risk subjects were recruited either from STD clinics in hospitals or district brothels in West Bengal in eastern India. Specifically, 270 pre-screened samples from this population were used in this study; 51 of the 270 samples (18.9%) were known to be negative by the QIAGEN hc2 test. Fifty Low Risk subjects with no known predisposition to disease were recruited from a health camp in Mumbai. Fifty urine samples were obtained from pregnant women from a general population in India. Cytological specimens and urine samples were obtained according to the protocol reviewed by independent ethics committees including the Indian Council of Medical Research, and with informed consent of the subjects. Urine was collected in commercially available collection cups. Urine samples were brought to at least 50 mM EDTA, shipped on dry ice and stored at −80° C. until further use.

Pap Smear and hc2 Test

Pap smears and hc2 tests were performed by Simbiosys Biowares Inc. and Metropolis Inc. A portion of the collected cervical sample was immediately used to make a smear for Pap testing and the remainder was transferred to buffer solution for HPV testing by QIAGEN hc2. hc2 tests were performed and analyzed as per manufacturer's instructions using the HR HPV Probe cocktail. The recommended positivity threshold of 1 μg/ml was used as a cutoff, and all samples with a relative light units/control (RLU/CO) ratio of 1.00 or greater were considered positive.

DNA Isolation

Urine samples stored at −80° C. were thawed and mixed by gentle inversion. DNA isolation was carried out as per the protocol described previously (Shekhtman E. M. et al. Clin Chem 2009; 55:723-729). Briefly a 1:1 urine:water sample was incubated with Q-sepharose resin slurry (GE Healthcare, Piscataway, N.J.). The resin was pelleted and the supernatant was discarded. Pelleted resin was resuspended and transferred to a spin column. The resuspension buffer was removed and the resin was washed. DNA was eluted from the resin by 2M LiCl. The eluate was brought to 70% ethanol and applied to a QIAquick column (QIAGEN, Hilden, Germany) The column was washed with 2M LiCl/70% EtOH followed by 75 mM KOAc (pH 5.0)/80% EtOH. DNA was eluted with EB Buffer (QIAGEN, Hilden, Germany) and stored at −20° C. The isolated DNA samples were quantitated by the Picogreen assay (Life Technologies).

PCR and Detection

Primers XEN-HPV-FAM-F and XEN-HPV-R (Table 6) were used in PCR assays. Following a 10 min treatment with AmpErase® UNG (Life Technologies), amplifications were carried out for 40 cycles in 25 µL with 600 nM each primer, 3 mM MgCl$_2$, 1.25 Units AmpliTaq Gold DNA Polymerase (Life Technologies), 200 µM each of dATP, dCTP, dGTP; and 400 µM dUTP. Each cycle was 15 seconds (s) at 95° C. and 60 s at 50° C. Reaction products were subjected to capillary electrophoresis by GENEWIZ (South Plainfield, N.J.).

DNA Sequencing

PCR amplifications were performed using different primer sets (Table 6) with JumpStart™ Taq DNA polymerase (Sigma-Aldrich) and various MgCl$_2$ concentrations (2 mM for MY09/MY11 and GP5+/GP6+, 3 mM for XEN-HPV-F/-R). Reaction mixtures were subjected to various cycling steps for each primer pair: 95° C. for 30 seconds, 55° C. for 45 seconds, 72° C. for 20 seconds, 37 cycles of amplification (MY09/MY11); 95° C. for 15 seconds, 40° C. for 30 seconds, 72° C. for 10 seconds, 50 cycles of amplification (GP5+/GP6+); 95° C. for 15 seconds, 50° C. for 60 seconds, 45 cycles of amplification (XEN-HPV-F/-R). PCR products were analyzed by electrophoresis on 10% polyacrylamide gels (Bio-Rad). Gel slices were excised and purified according to QIAEX II Gel Extraction Kit instructions (QIAGEN) and sequenced with one of the primers used for PCR amplification. DNA sequencing was performed by GENEWIZ Inc. (South Plainfield, N.J.). Raw PCR product sequences were analyzed by NCBI Blastn algorithm to match specific human papillomavirus strains.

Statistical Analysis

The data were analyzed using standard contingency table methods (Excel 2003, Microsoft Corp.). To characterize the utility of our method, we calculated its concordance with either hc2 test and/or sequencing and diagnostic sensitivity, specificity, as well as positive and negative predictive values (PPV and NPV) (Altman, D. G. and Bland, J. M. BMJ 1994; 309:102). The 95% confidence interval was calculated by JavaStat for each of the above parameters. Marginal homogeneity between the analysis methods being compared was assessed by the McNemar's test ($X^2$). P values of <0.05 were considered statistically significant. Agreement between tests was assessed using Cohens kappa statistic (K). K values between 0.4-0.6 were considered as having moderate agreement and values of 0.61-0.8 were considered as having considerable agreement (Landis, J R; Koch, G G. Biometrics. 1977; 33:159-174. doi: 10.2307/2529310).

specimen results of hc2 assay and Pap test. Results of comparison with hc2 are shown in Table 7. The concordance was 248/320 (77.5%). Of the 320 urine samples, 72 gave discordant results with the matched cervical specimen hc2 assay and were further examined by DNA sequencing.

DNA Sequencing of Discordants

Alternative amplification and sequencing was first attempted using the primers MY09/MY11 which produce a product of about 450 bp. If no high risk HPV product could be obtained or sequenced, then sequencing was attempted using the GP5+/GP6+ primers to generate a fragment of about 150 bp. Both of these primer pairs examine the HPV L1 region, a site independent from that used for HPV detection by the CE assay. In cases when the MY09/MY11 and/or GP5+/GP6+ primers generated only sequences of low risk HPV or did not generate specific product, XEN-HPV-F/-R primers were used to amplify an 88 by footprint of the E1 gene that could provide evidence of high risk HPV DNA sequence if any were present in the sample.

Of the 38 discordant samples Reactive by CE and Nonreactive by hc2, High Risk HPV types were demonstrated by DNA sequencing of the L1 region (MY09/MY11 and/or GP5+/GP6+ primers) in 18 (47.4%) samples. Additionally further 13 samples were shown to have High Risk HPV by using XEN-HPV-F/-R primers, making a total of 31/38 (81.6%) containing High Risk HPV (Table 8).

Of the 34 discordant samples Reactive by hc2 but Nonreactive by CE, High Risk HPV types were demonstrated by DNA sequencing of the L1 region (MY09/MY11 and/or GP5+/GP6+ primers) in four samples. Six additional samples were shown to have high risk HPV types by using XEN-HPV-F/-R primers. These latter primers failed to detect the sample by CE but amplified a product for sequencing possibly because of low titer of HPV. This may be because PCR using XEN-HPV-F/-R primers for detection was carried out for 40 cycles vs. 45 cycles for sequencing. The latter six samples when amplified using the MY09/11 and/or GP5+/GP6+ primer pairs yielded either no HPV product or a low risk type. In all, 10 out of 34 (29.4%) samples Reactive by hc2 but not by CE were shown to contain High Risk HPV (Table 8).

The use of XEN-HPV-F/-R primers in conjunction with sequencing results indicate that the hc2 assay generated both more False Positive and False Negative results (Table 8) than the CE test. Concordance of Xenomics and hc2 tests with sequencing results for this group of patients is 55/72 (76.4%) and 17/72 (23.6%), respectively. The CE assay did not detect 5 samples with HPV16, one HPV18, one HPV33, one

TABLE 6

| Primer | Sequence | SEQ ID NO: |
|---|---|---|
| XEN-HPV-FAM-F | 5'-FAM-CAG GCA GAA TTA GAG RCA GC-3' | 98 |
| XEN-HPV-F | 5'-CAG GCA GAA TTA GAG RCA GC-3' | 99 |
| XEN-HPV-R | 5'-TCC ACC ACA WAC TTT CGT TTT A-3' | 100 |
| MY09 | 5'-CGT CCM ARR GGA WAC TGA TC-3' | 101 |
| MY11 | 5'-GCM CAG GGW CAT AAY AAT GG-3' | 102 |
| GP5+ | 5'-TTT GTT ACT GTG GTA GAT ACT AC-3' | 103 |
| GP6+ | 5'-GAA AAA TAA ACT GTA AAT CAT ATT C-3' | 104 |

Results

A total of 320 urine samples were analyzed by the Xenomics CE assay for comparison with corresponding cervical HPV35, one HPV51, and one containing multiple High Risk HPV types (16+33) (Table 9). However since it detected other samples with each type except HPV51, these False Negatives may be due to low titer (Table 10). We did not find other examples of HPV51 in our patient sample set, but it should be noted that HPV51 was amplified and sequenced only by using XEN-HPV-F/-R primers.

In comparison, the hc2 assay did not detect 13 samples with HPV16, six HPV18, one HPV31, one HPV35, two HPV45, one HPV52, one HPV58, and two HPV59 and four containing multiple high risk HPV types (16+45, 16+33, 16+56 and 18+31) (Table 10). 31 out of 38 (81.6%) samples Nonreactive by the hc2 test contained High Risk HPV. Table 11 lists the 13 of the 31 samples which required using XEN-HPV-F/-R primers for high risk types to be revealed.

Secondary sequencing with the L1 region primers (MY09/MY11 and/or GP5+/GP6+ primers) yielded either no HPV detected or low risk types.

Low Risk Samples

The CE assay detected more High Risk HPV positive women, including many flagged as ASCUS and Normal, than the hc2 assay (Table 10). Some samples provided by Simbiosys were categorized as Control with a normal Pap result but no available hc2 result. Others were flagged as Normal by Pap smear and were Nonreactive by hc2. Samples from these groups were obtained from high-risk populations including STD clinics and brothels. We tested 50 samples designated by Metropolis as Low Risk with a clinical diagnosis of Normal or non-malignant. 3 out of 50 (6.0%) were Reactive by hc2, and six (12.0%) were Reactive by CE. Of these latter six samples, four contained High Risk HPV (types 16, 18, and 31) by sequencing and two contained no evidence of HPV DNA.

To further examine prevalence of HPV infection in a presumed low-risk population, we assayed 50 urine samples from pregnant women obtained from a general population in India. Pap and hc2 results were not available from these patients. Out of the 50, one was Reactive by the Xenomics CE assay. DNA sequencing confirmed that this sample contained High-Risk HPV45.

TABLE 7

Contingency table of hc2 High-Risk HPV DNA Test (QIAGEN) vs. Xenomics CE test.

| Xenomics CE | No. samples with hc2 result[a] | | |
|---|---|---|---|
| HPV test result | Reactive | Nonreactive | Total |
| Reactive | 102 | 38 | 140 |
| Nonreactive | 34 | 146 | 180 |
| Total | 136 | 184 | 320 |

[a]Concordance 77.5% (248/320; CI 95%, 72-81%; p = 0.7), Sensitivity 75.0% (102/136; CI 95%, 68.2-79%), Specificity 79.3% (146/184; CI 95%, 75.2-83%), PPV 72.9% (102/140; CI 95%, 67-77%), NPV 81.1% (146/180; CI 95%, 76-84%), K = 0.53.

TABLE 8

Contingency table of Xenomics CE/hc2 discordants vs. DNA sequencing.

| CE/hc2 HPV test results | No. samples with High Risk[b] HPV DNA by Sequencing | | |
|---|---|---|---|
| | Positive | Negative | Total |
| CE+/hc2− | 31 | 7 | 38 |
| CE−/hc2+ | 10 | 24 | 34 |
| Total | 41 | 31 | 72 |

[b]Concordance 76.4% (55/72; CI 95%, 65-84%; p = 0.6), Sensitivity 75.6% (31/41; CI 95%, 66-82%), Specificity 77.4% (24/31; CI 95%, 64-82%), PPV 81.6% (31/38; CI 95%, 71-89%), NPV 70.6% (24/34; CI 95%, 59-79%), K = 0.52.

TABLE 9

Sequencing, Pap and cancer staging data for samples nonreactive by Xenomics CE test.

| Pap Result | No. of Samples hc2 Reactive/CE Nonreactive | HPV Genotype[a] |
|---|---|---|
| Stage IVA | 1 | No HPV detected |
| Stage IIIB | 3 | 74, 61 + 16, 16 + 33 |
| Stage IIIA | 2 | No HPV detected (2) |
| Stage IIB | 1 | No HPV detected |
| Stage IB | 2 | Unknown Low risk HPV, 16 |
| CIN III | 2 | No HPV detected, 16 |
| CIN II | 3 | No HPV detected, 16, 33 |
| CIN I | 8 | 6 + 18, 84, 66, 53, 35, No HPV detected (3) |
| LSIL | 1 | No HPV detected |
| ASCUS | 9 | 6, 16, 51, 53, No HPV detected (5) |
| Normal | 2 | No HPV detected (2) |

[a]High-Risk target genotypes are shown in bold. Numbers in parentheses refer to number of cases.

TABLE 10

Sequencing, Pap and cancer staging data for samples reactive by Xenomics CE and non-reactive by the hc2 test.

| Pap result | No. of Samples CE Reactive/hc2 Nonreactive | HPV Genotype[a] |
|---|---|---|
| ASCUS | 10 | 16 (7), 18, 45, 58 |
| ASCUS | 3 | 6 + 59, 70 + 35, 81 + 45 |
| ASCUS | 1 | 6 |
| ASCUS | 1 | 81 |
| ASCUS | 1 | No HPV detected |
| Normal | 7 | 16 (3), 18 (3), 31 (1) |
| Normal | 4 | 16 + 45, 61 + 59, 6 + 16, 32 + 52 |
| Normal | 1 | 6 + 18 + 97 |
| Normal | 3 | No HPV detected |
| Control | 1 | 18 |
| Control | 1 | 16 + 33 |
| Control | 1 | 70 |
| Stage IIB | 3 | 16, 16 + 56, 18 + 31 + 45 |
| Stage IIIB | 1 | 16 |

[a]High-Risk target genotypes are shown in bold. Numbers in parentheses refer to number of cases.

TABLE 11

Sequencing of High Risk HPV samples which were hc2 test nonreactive, CE test reactive, and detected only by the E1 region primer pair XEN-HPV-F/R.

| Sample ID | Clinical diagnosis | hc2 test result | CE test result | High Risk HPV Type determined by sequencing[a] | Primers for secondary sequencing | HPV Type from secondary sequencing[b] |
|---|---|---|---|---|---|---|
| BW-117 | Normal | neg | pos | 59 | MY09/11 | 61 |
| BW-170 | Normal | neg | pos | 16 | MY09/11 | 6 |
| BW-176 | Normal | neg | pos | 18 | MY09/11 | 6 |
| MI-00051 | Normal | neg | pos | 16 | MY09/11 | Type undetermined |
| MI-00064 | Normal | neg | pos | 18 | MY09/11 | negative |
| MI-00071 | Normal | neg | pos | 31 | MY09/11 | negative |
| BW-154 | Normal | neg | pos | 52 | MY09/11, GP5+/6+ | negative, 32 |
| BW-109 | ASCUS | neg | pos | 45 | MY09/11 | CY11-456/81 |
| BW-159 | ASCUS | neg | pos | 59 | MY09/11 | 6 |
| BW-172 | ASCUS | neg | pos | 35 | MY09/11 | 70 |
| S-G (P3) | II B | neg | pos | 18/31, 45 | GP5+/6+ | negative |
| M-B (P4) | IIB | neg | pos | 16 | MY09/11 | Type undetermined |
| UD (P18) | III B | neg | pos | 16 | MY09/11 | Type undetermined |

[a]Sequencing done using primers Xen-HPV-F/R. High-Risk target genotypes are shown in bold.
[b]Sequencing done using literature primers MY09/11 and/or GP5+/6+.

The feasibility of using urine as a sample matrix for detecting High Risk HPV was examined. The Xenomics HPV test could therefore be proposed as a qualitative screening test thereby eliminating the need of Pap test or other molecular tests for screening.

The concordance of the xenomics HPV test when compared with the hc2 test was 77.5% (248/320, K=0.5; p=0.7), with overall Sensitivity and Specificity 75.0% (102/136) and 79.3% (146/184) respectively (Table 7). The kappa coefficient of 0.5 indicates moderate agreement between the two tests. Of the 320 urine samples analyzed, 72 gave discordant results with the cervical specimen-based hc2 assay and were further examined by DNA sequencing for resolution. With DNA sequencing being used as the gold standard, the CE test was more sensitive and specific with a demonstrated False Negative and False Positive rate of 10/180 (5.6%) and 7/140 (5.0%) respectively. The hc2 assay in comparison had a False Negative and False Positive rate of 31/184 (16.8%) and 24/136 (17.6%) respectively (Tables 7 and 8).

Most of the samples Nonreactive by the hc2 test and Reactive by the Xenomics test were of either ASCUS or Normal cytology by the Pap test. HPV types 16, 18 and 45 accounted for 16/38 (42%), 7/38 (18.4%) and 4/38 (10.5%) of the samples missed. Prevalence of high-risk human papillomavirus type 16/18 infection among women with normal cytology in Indian populations has been previously reported (Gupta S. et al. Cytopathology 2008; doi: 10.111/j.1365-2303.2008.00611) Overall HPV prevalence among cytologically normal women in that study was 16.6%. HPV16 was detected in 10.1%, whereas HPV18 was detected in 1% of women. Previously also reported was the finding that the QIAGEN hc2 test has lower High Risk HPV detection in women over 30 years of age with normal or CIN1 cytology when compared with the other PCR based tests (Stevens M.P. et al. J Clin Microbiol 2007 ; 45:2130-2137. More than 80% of our sampling population was also over 30 years of age.

Some samples normal by Pap test and Nonreactive by hc2 test but Reactive by the Xenomics test had mixed infections with high and low risk HPV types. This reinforces the notion that our primers targeting the E1 region of HPV can detect High Risk HPV under conditions when standard tests currently in use cannot. The inability of primers targeting the L1 region to detect certain high risk HPV types (HPV 48, 51, 52, 68) has been previously reported (Depuydt C. E. et al. J Cell Mol Med 2007; 11:881-891). This may be explained by deletion of the L1 region in these samples. Alternatively the MY09/MY11 and GP5+/GP6+ primer pairs are non-specific; hence the presence or abundance of low-risk HPV types may confound attempts to sequence any underlying high risk HPV.

The Xenomics HPV test was unable to detect High Risk HPV types in 10 hc2-Reactive samples confirmed by DNA sequencing (Table 9). Six out of the 10 samples were staged CIN 2 and higher. One possible explanation is the deletion of the HPV E1 region (Arias-Pulido H. et al. J Clin Microbiol 2006; 44:1755-1762). In 3 of the 6 samples, only XEN-HPV-F/-R primers generated a PCR product that, upon sequencing, contained High Risk HPV. XEN-HPV-F/-R primers confirmed the presence of High Risk HPV33 in a fourth sample. This indicates that the E1 region was hence not deleted. The PCR conditions used for sequencing as opposed to detection, including JumpStart DNA polymerase and cycle number, may provide a more sensitive amplification system. The HPV DNA CE assay balances sensitivity and specificity such that some low titer HPV samples may not be detected. The result is an assay with fewer false positive and false negative results compared to a commercially available assay.

Table 12 considers the assay comparison when the hc2 result is combined with DNA sequencing using both literature primers (MY09/MY11 and/or GP5+/GP6+ primers) and XEN-HPV-F/-R primers to resolve discordant samples. In this case, the concordance is 94.7% (303/320, K=0.89, p=0.6). The assay Sensitivity is 93.0% (133/143); Specificity is 96.0% (170/177). Positive and Negative Predictive Values are 95.0% (133/140) and 94.4% (170/180), respectively. The Kappa value of 0.89 indicates excellent agreement between the two methods. Hence the QIAGEN hc2 test combined with sequencing results using primers targeting both the L1 and the E1 regions of the HPV genome appears equivalent to our CE assay (p=0.6).

Thus, sensitivity of urine-based HPV testing is similar to or better than the currently used hc2 test based on analysis of cervical cells. A higher sensitivity of the CE test compared to other urine DNA-based studies can be explained by several factors. First, in our experiments DNA was isolated from whole urine, not a cellular fraction. This is critical in the overall recovery of HPV DNA. In addition to crossing over chromatin fragments from dying cervical cells, HPV DNA sequences can also be contributed by transrenal DNA (Tr-DNA) (Melkonyan H. S. et al. Ann N Y Acad Sci 2008; 1137:73-81). This statement is supported by the fact that in sequencing experiments our primers designed to amplify shorter amplicons (88 bp) detected more High Risk HPV than the MY09/MY11 primers designed to amplify a larger 450 by amplicon. These results also demonstrate that use of a shorter DNA target for PCR increases sensitivity of HPV detection in urine samples. Second, the Q-resin-based technique for urinary DNA is more effective for isolation of short DNA fragments than silica-based methods.

Some High Risk HPV detection differences may arise from the comparison of urine and cervical cell sampling. Unfortunately, cervical cells were not available in this study for direct comparison. One might postulate that some samples Nonreactive by the CE assay could be the result of different hygiene rules applied to hospital patients.

Numerous reports have been published comparing the hc2 assay to other molecular assays, however, all of these assays are based on cervical cells from patients. This is a first report detecting HPV DNA from urine using primers targeting the E1 region of the HPV genome. This report also raises questions about the use of Pap and hc2 tests in screening for High Risk HPV in women in India and other developing countries. Incidence and mortality from cervical cancer have remained largely uncontrolled in these countries, mostly because of the lack or ineffectiveness of screening programs. Since non-invasiveness and simplicity of sample collection are important for acceptance of screening tests, use of simple urine collection instead of cervical cell scraping can enhance implementation of HPV screening tests for cervical cancer both in developed and developing countries.

TABLE 12

Combination of DNA Sequencing with hc2 results compared to CE assay results: Inclusion of literature primers (MY09/MY11 and/or GP5+/GP6+ primers) and XEN- HPV-F/R primer sequencing results to resolve CE/hc2 discordant results.

| Xenomics CE | Evidence for presence of high risk HPV*[b] | | |
|---|---|---|---|
| HPV test result | Positive | Negative | Total |
| Reactive | 133 | 7 | 140 |
| Nonreactive | 10 | 170 | 180 |
| Total | 143 | 177 | 320 |

[b]Concordance 94.7% (303/320; CI 95%, 91.7-96.6%; p = 0.6), Sensitivity 93.0% (133/143; CI 95%, 89.6-95%), Specificity 96.0% (170/177; CI 95%, 93.3-97.8%), PPV 95.0% (133/140; CI 95%, 91.6-97%), NPV 94.4% (170/180; CI 95%, 91.8-96%), K = 0.89.
*Evidence consists of an hc2 Reactive result and/or presence of High Risk HPV as demonstrated by DNA sequencing.

We claim:

1. An oligonucleotide having the sequence 5'-CAGGCA-GAATTAGAGRCAGC (SEQ ID NO:41 or 99), wherein R is A or G, and the oligonucleotide is optionally labeled.

2. The oligonucleotide according to claim 1, wherein the oligonucleotide is fluorescently labeled.

3. The oligonucleotide according to claim 2, wherein the oligonucleotide is XEN-HPV-FAM-F (SEQ ID NO:98).

4. A pair of oligonucleotide primers comprising a forward primer that is the oligonucleotide of claim 1 and a reverse primer having the sequence 5'-TCCACCA-CAWACTTTCGTTTTA (SEQ ID NO:42 or 100), wherein W is T or A.

5. The oligonucleotide primers according to claim 4, wherein the forward primer is fluorescently labeled.

6. The oligonucleotide primers according to claim 5, wherein the forward primer is XEN-HPV-FAM-F (SEQ ID NO:98) and the reverse primer is XEN-HPV-R (SEQ ID NO:100).

7. A kit comprising the oligonucleotide according to claim 1.

8. A kit comprising the oligonucleotide according to claim 2.

9. A kit comprising the oligonucleotide according to claim 3.

10. A kit comprising the oligonucleotide primers according to 4.

11. A kit comprising the oligonucleotide primers according to 5.

12. A kit comprising the oligonucleotide primers according to 6.

13. An oligonucleotide primer having the sequence 5'-TCCACCACAWACTTTCGTTTTA (SEQ ID NO:42 or 100), wherein W is T or A.

14. A method of detecting human papillomavirus (HPV) infection in a patient, the method comprising:

detecting one or more sequences of the E1 gene of HPV in a urine sample obtained from a patient, wherein said detecting comprises hybridization of said one or more sequences to the oligonucleotide of claim 1 and wherein detection of one or more sequences of the E1 gene of HPV indicates the presence of at least one HPV infection in a patient.

15. The method of claim 14, wherein said amplifying comprises a technique selected from the polymerase chain reaction (PCR); nested primer PCR; Real Time PCR; NA hybridization; Cyclic Probe Reaction; Single-Strand Conformation Polymorphism (SSCP); Strand Displacement Amplification (STA); and Restriction Fragment Length Polymorphism (RFLP).

16. The method of claim 14, wherein said detecting comprises
(a) amplifying nucleic acids, from said urine sample obtained from a patient, with said oligonucleotide as a forward primer to produce amplified E1 gene sequences; and
(b) detecting the amplified E1 gene sequences.

17. The method of claim 16, wherein said amplifying further comprises an oligonucleotide having the sequence 5'-TCCACCACAWACTTTCGTTTTA (SEQ ID NO:42 or 100), wherein W is T or A.

18. The method of claim 17, wherein said amplifying comprises XEN-HPV-FAM-F (SEQ ID NO:98) and XEN-HPV-R (SEQ ID NO:100) as primers.

19. The method of claim 14, wherein said nucleic acids comprise transrenal DNA.

20. The method of claim 14, further comprising reducing nucleic acid degradation in the urine sample.

21. The method of claim 20, wherein reducing nucleic acid degradation comprises inhibiting nuclease activity by increased pH, increased salt concentration, heat inactivation, or by treating said urine sample with a compound selected from the group consisting of: ethylenediaminetetraacetic acid, guanidine-HCl guanidine isothiocyanate, N-lauroylsarcosine, and sodium dodecylsulphate.

22. The method of claim 14, further comprising substantially isolating said nucleic acids from the urine sample before said amplifying.

23. The method of claim 22, wherein said isolating is by precipitation or using a solid adsorbent material.

24. The method of claim 14, further comprising the step of quantifying said amplified E1 gene sequences.

25. The method of claim 14, wherein said detecting further comprises the extension of said oligonucleotide after hybridization.

* * * * *

SEQUENCE LISTING

<160> NUMBER OF SEQ ID NOS: 103

<210> SEQ ID NO 1
<211> LENGTH: 149
<212> TYPE: DNA
<213> ORGANISM: Human papillomavirus

<400> SEQUENCE: 1

```
cagtgataca ggtgaagatt tggtagattt tatagtaaat gataatgatt atttaacaca      60
ggcagaaaca gagacagcac atgcgttgtt tactgcacag gaagcaaaac aacatagaga     120
tgcagtacag gttctaaaac gaaagtatt                                       149
```

<210> SEQ ID NO 2
<211> LENGTH: 149
<212> TYPE: DNA
<213> ORGANISM: Human papillomavirus

<400> SEQUENCE: 2

```
aacagacaca gggtcggata tggtagattt tattgataca caaggaacat tttgtgaaca      60
ggcagagcta gagacagcac aggcattgtt ccatgcgcag gaggtccaca atgatgcaca     120
agtgttgcat gtttttaaaac gaaagtttg                                      149
```

<210> SEQ ID NO 3
<211> LENGTH: 149
<212> TYPE: DNA
<213> ORGANISM: Human papillomavirus

<400> SEQUENCE: 3

```
tagtgatact ggggaggata tggttgactt tattgacaat gtaatgtat acaacaatca       60 ggcagaagca gagacagcac aggcattgtt tcatgcacag gaagcggagg aacatgcaga    120
```

```
ggctgtgcag gttctaaaac gaaagtatg                                    149
```

<210> SEQ ID NO 4
<211> LENGTH: 149
<212> TYPE: DNA
<213> ORGANISM: Human papillomavirus

<400> SEQUENCE: 4

```
agatgacagt ggcacggatt tactagagtt tatagatgat tctatggaaa atagtataca   60
ggcagacaca gaggcagccc gggcattgtt taatatacag gaaggggagg atgatttaaa  120
tgctgtgtgt gcactaaaac gaaagtttg                                    149
```

<210> SEQ ID NO 5
<211> LENGTH: 149
<212> TYPE: DNA
<213> ORGANISM: Human papillomavirus

<400> SEQUENCE: 5

```
ctgtgacagg ggggaggata tggtggactt tataaatgat acagatatat taaacataca   60
ggcagaaaca gagacagcac aagcattatt tcatgcacag gaggagcaaa cacacaaaga  120
ggctgtacag gtcctaaaac gaaagtatg                                    149
```

<210> SEQ ID NO 6
<211> LENGTH: 149
<212> TYPE: DNA
<213> ORGANISM: Human papillomavirus

<400> SEQUENCE: 6

```
aacagataca ggttcagacc tggcagactt tattgatgat tccacagata tttgtgtaca   60
ggcagagcgt gagacagcac aggtactttt acatatgcaa gaggcccaaa gggatgcaca  120
agcagtgcgt gccttaaaac gaaagtata                                    149
```

<210> SEQ ID NO 7
<211> LENGTH: 149
<212> TYPE: PRT
<213> ORGANISM: Human papillomavirus

<400> SEQUENCE: 7

```
Ala Ala Cys Ala Gly Ala Thr Ala Cys Ala Gly Gly Thr Cys Gly
  1               5                  10                  15

Gly Ala Thr Ala Thr Gly Gly Thr Ala Gly Ala Thr Thr Thr Ala
                 20                  25                  30

Thr Thr Gly Ala Cys Ala Cys Ala Cys Ala Thr Thr Ala Thr Cys
         35                  40                  45

Cys Ala Thr Thr Thr Gly Thr Gly Ala Ala Cys Ala Gly Gly Cys Ala
     50                  55                  60

Gly Ala Gly Cys Ala Ala Gly Ala Gly Ala Cys Ala Gly Cys Ala Cys
 65                  70                  75                  80

Ala Gly Gly Cys Ala Thr Thr Gly Thr Thr Cys Cys Ala Thr Gly Cys
                 85                  90                  95

Gly Cys Ala Gly Gly Ala Ala Gly Thr Thr Cys Ala Gly Ala Ala Thr
                100                 105                 110

Gly Ala Thr Gly Cys Ala Cys Ala Gly Gly Thr Gly Thr Thr Gly Cys
                115                 120                 125

Ala Thr Cys Thr Thr Thr Ala Ala Ala Cys Gly Ala Ala Ala
                130                 135                 140

Gly Thr Thr Thr Gly
```

<210> SEQ ID NO 8
<211> LENGTH: 149
<212> TYPE: DNA
<213> ORGANISM: Human papillomavirus

<400> SEQUENCE: 8

```
agatgataca ggatctgatt taataaactt tatagatagt gaaactagta tttgcagtca    60
ggcggaacag gagacagcac gggcgttgtt tcaggcccaa gaattacagg caaacaaaga   120
ggctgtgcat cagttaaaac gaaagtttc                                     149
```

<210> SEQ ID NO 9
<211> LENGTH: 149
<212> TYPE: DNA
<213> ORGANISM: Human papillomavirus

<400> SEQUENCE: 9

```
atatgatagt ggaacagatc taatagattt tatagatgat tcaaatataa ataatgaaca    60
ggcagaacat gaggcagccc gggcattgtt taatgcacag gaagggagg atgatttaca    120
tgctgtgtct gcagtaaaac gaaagttta                                     149
```

<210> SEQ ID NO 10
<211> LENGTH: 148
<212> TYPE: DNA
<213> ORGANISM: Human papillomavirus

<400> SEQUENCE: 10

```
ggatgaaata gatacagatt tagatggatt tatagacgat tcatatatac aaaatataca    60
ggcagacgca gaaacagtca acaattgttg caagtacaaa cagcacatgc agataaacag   120
acgttgcaaa aactaaaacg aaagtata                                      148
```

<210> SEQ ID NO 11
<211> LENGTH: 149
<212> TYPE: DNA
<213> ORGANISM: Human papillomavirus

<400> SEQUENCE: 11

```
agacgatagt ggtacagatt taatagagtt tatagatgat tcagtacaaa gtactacaca    60
ggcagaagca gaggcagccc gagcgttgtt taatgtacag gaaggggtgg acgatataaa   120
tgctgtgtgt gcactaaaac gaaagtttg                                     149
```

<210> SEQ ID NO 12
<211> LENGTH: 149
<212> TYPE: DNA
<213> ORGANISM: Human papillomavirus

<400> SEQUENCE: 12

```
aacagataca ggttcagact tggtagattt tattgatgat accacaacaa tttgtgtaca    60
ggcagagcgc gagacagcac aggccttgtt taatgtgcag gaagcccaaa gggatgcacg   120
ggaaatgcat gttttaaaac gaaagtttg                                     149
```

<210> SEQ ID NO 13
<211> LENGTH: 149
<212> TYPE: DNA
<213> ORGANISM: Human papillomavirus

<400> SEQUENCE: 13
aaatgataca gggtctgata taatagactt tatagataca aataacagta tttgcagtca    60
ggcggaacaa gagacagcac gggcgttgtt tcaggtccaa gaaacacagg cacacaaaga   120
ggctgcacag catctaaaac gaaagtttt                                    149

<210> SEQ ID NO 14
<211> LENGTH: 142
<212> TYPE: DNA
<213> ORGANISM: Human papillomavirus

<400> SEQUENCE: 14
ggtggaggac agtgggtatg acatggtgga ctttattgat gacagcaata ttacacacaa    60
ttcactggaa gcacaggcat tgtttaacag gcaggaggcg gacacccatt atgcgactgt   120
gcaggaccta aaacgaaagt at                                           142

<210> SEQ ID NO 15
<211> LENGTH: 142
<212> TYPE: DNA
<213> ORGANISM: Human papillomavirus

<400> SEQUENCE: 15
ggtggaggac agtgggtatg acatggtgga ctttattgat gacaggcata ttacacaaaa    60
ttctgtggaa gcacaggcat tgtttaatag gcaggaggcg gatgctcatt atgcgactgt   120
gcaggaccta aaacgaaagt at                                           142

<210> SEQ ID NO 16
<211> LENGTH: 19
<212> TYPE: DNA
<213> ORGANISM: Artificial Sequence
<220> FEATURE:
<223> OTHER INFORMATION: Primer sequence

<400> SEQUENCE: 16
caggcagaaa cagagacag                                                19

<210> SEQ ID NO 17
<211> LENGTH: 19
<212> TYPE: DNA
<213> ORGANISM: Artificial Sequence
<220> FEATURE:
<223> OTHER INFORMATION: Primer sequence

<400> SEQUENCE: 17
csggcagagc tagagacag                                                19

<210> SEQ ID NO 18
<211> LENGTH: 19
<212> TYPE: DNA
<213> ORGANISM: Artificial Sequence
<220> FEATURE:
<223> OTHER INFORMATION: Primer sequence

<400> SEQUENCE: 18
caggcagaag cagagacag                                                19

<210> SEQ ID NO 19
<211> LENGTH: 19
<212> TYPE: DNA
<213> ORGANISM: Artificial Sequence
<220> FEATURE:
<223> OTHER INFORMATION: Primer sequence

<400> SEQUENCE: 19

-continued caggcagaca cagaggcag                                             19

<210> SEQ ID NO 20
<211> LENGTH: 19
<212> TYPE: DNA
<213> ORGANISM: Artificial Sequence
<220> FEATURE:
<223> OTHER INFORMATION: Primer sequence

<400> SEQUENCE: 20
caggcagagc gtgagacag                                             19

<210> SEQ ID NO 21
<211> LENGTH: 19
<212> TYPE: DNA
<213> ORGANISM: Artificial Sequence
<220> FEATURE:
<223> OTHER INFORMATION: Primer sequence

<400> SEQUENCE: 21
caggcagagc aagagacag                                             19

<210> SEQ ID NO 22
<211> LENGTH: 19
<212> TYPE: DNA
<213> ORGANISM: Artificial Sequence
<220> FEATURE:
<223> OTHER INFORMATION: Primer sequence

<400> SEQUENCE: 22
caggcggaac aggagacag                                             19

<210> SEQ ID NO 23
<211> LENGTH: 19
<212> TYPE: DNA
<213> ORGANISM: Artificial Sequence
<220> FEATURE:
<223> OTHER INFORMATION: Primer sequence

<400> SEQUENCE: 23
caggcagaac atgaggcag                                             19

<210> SEQ ID NO 24
<211> LENGTH: 19
<212> TYPE: DNA
<213> ORGANISM: Artificial Sequence
<220> FEATURE:
<223> OTHER INFORMATION: Primer sequence

<400> SEQUENCE: 24
caggcagacg cagaaacag                                             19

<210> SEQ ID NO 25
<211> LENGTH: 19
<212> TYPE: DNA
<213> ORGANISM: Artificial Sequence
<220> FEATURE:
<223> OTHER INFORMATION: Primer sequence

<400> SEQUENCE: 25
caggcagaag cagaggcag                                             19

<210> SEQ ID NO 26
<211> LENGTH: 20
<212> TYPE: DNA
<213> ORGANISM: Artificial Sequence
<220> FEATURE:

<223> OTHER INFORMATION: Primer sequence

<400> SEQUENCE: 26
caggcagagc gdcgagacag                                               20

<210> SEQ ID NO 27
<211> LENGTH: 19
<212> TYPE: DNA
<213> ORGANISM: Artificial Sequence
<220> FEATURE:
<223> OTHER INFORMATION: Primer sequence

<400> SEQUENCE: 27
caggcggaac aagagacag                                                19

<210> SEQ ID NO 28
<211> LENGTH: 23
<212> TYPE: DNA
<213> ORGANISM: Artificial Sequence
<220> FEATURE:
<223> OTHER INFORMATION: Primer sequence

<400> SEQUENCE: 28
tgcttcctgt gcagtaaaca acg                                           23

<210> SEQ ID NO 29
<211> LENGTH: 23
<212> TYPE: DNA
<213> ORGANISM: Artificial Sequence
<220> FEATURE:
<223> OTHER INFORMATION: Primer sequence

<400> SEQUENCE: 29
gacctcctgc gcatggaaca atg                                           23

<210> SEQ ID NO 30
<211> LENGTH: 23
<212> TYPE: DNA
<213> ORGANISM: Artificial Sequence
<220> FEATURE:
<223> OTHER INFORMATION: Primer sequence

<400> SEQUENCE: 30
cgcttcvtgt gcatgaaaca atg                                           23

<210> SEQ ID NO 31
<211> LENGTH: 23
<212> TYPE: DNA
<213> ORGANISM: Artificial Sequence
<220> FEATURE:
<223> OTHER INFORMATION: Primer Sequence

<400> SEQUENCE: 31
cccttcctgt atattaaaca atg                                           23

<210> SEQ ID NO 32
<211> LENGTH: 23
<212> TYPE: DNA
<213> ORGANISM: Artificial Sequence
<220> FEATURE:
<223> OTHER INFORMATION: Primer sequence

<400> SEQUENCE: 32
ctcctcctgt gcatgaaata atg                                           23

<210> SEQ ID NO 33

```
<211> LENGTH: 24
<212> TYPE: DNA
<213> ORGANISM: Artificial Sequence
<220> FEATURE:
<223> OTHER INFORMATION: Primer sequence

<400> SEQUENCE: 33
ggcctcttgc atatgtaaaa gtac                                             24

<210> SEQ ID NO 34
<211> LENGTH: 23
<212> TYPE: DNA
<213> ORGANISM: Artificial Sequence
<220> FEATURE:
<223> OTHER INFORMATION: Primer sequence

<400> SEQUENCE: 34
aacttcctgc gcatggaaca atg                                              23

<210> SEQ ID NO 35
<211> LENGTH: 23
<212> TYPE: DNA
<213> ORGANISM: Artificial Sequence
<220> FEATURE:
<223> OTHER INFORMATION: Primer sequence

<400> SEQUENCE: 35
taattcttgg gcctgaaaca acg                                              23

<210> SEQ ID NO 36
<211> LENGTH: 23
<212> TYPE: DNA
<213> ORGANISM: Artificial Sequence
<220> FEATURE:
<223> OTHER INFORMATION: Primer sequence

<400> SEQUENCE: 36
cccttcctgt gcattaaaca atg                                              23

<210> SEQ ID NO 37
<211> LENGTH: 24
<212> TYPE: DNA
<213> ORGANISM: Artificial Sequence
<220> FEATURE:
<223> OTHER INFORMATION: Primer sequence

<400> SEQUENCE: 37
tgctgtttgt acttgcaaca attg                                             24

<210> SEQ ID NO 38
<211> LENGTH: 23
<212> TYPE: DNA
<213> ORGANISM: Artificial Sequence
<220> FEATURE:
<223> OTHER INFORMATION: Primer sequence

<400> SEQUENCE: 38
cccttcctgt acattaaaca acg                                              23

<210> SEQ ID NO 39
<211> LENGTH: 23
<212> TYPE: DNA
<213> ORGANISM: Artificial Sequence
<220> FEATURE:
<223> OTHER INFORMATION: Primer sequence

<400> SEQUENCE: 39
```

```
ggcttcctgc acattaaaca agg                                              23

<210> SEQ ID NO 40
<211> LENGTH: 23
<212> TYPE: DNA
<213> ORGANISM: Artificial Sequence
<220> FEATURE:
<223> OTHER INFORMATION: Primer sequence

<400> SEQUENCE: 40
tgtttcttgg acctgaaaca acg                                              23

<210> SEQ ID NO 41
<211> LENGTH: 20
<212> TYPE: DNA
<213> ORGANISM: Artificial Sequence
<220> FEATURE:
<223> OTHER INFORMATION: Primer sequence

<400> SEQUENCE: 41
caggcagaat tagagrcagc                                                  20

<210> SEQ ID NO 42
<211> LENGTH: 22
<212> TYPE: DNA
<213> ORGANISM: Artificial Sequence
<220> FEATURE:
<223> OTHER INFORMATION: Primer sequence

<400> SEQUENCE: 42
tccaccacaw actttcgttt ta                                               22

<210> SEQ ID NO 43
<211> LENGTH: 33
<212> TYPE: DNA
<213> ORGANISM: Artificial Sequence
<220> FEATURE:
<223> OTHER INFORMATION: Primer sequence

<400> SEQUENCE: 43
caactccatc tacacaggca gaaacagaga cag                                   33

<210> SEQ ID NO 44
<211> LENGTH: 33
<212> TYPE: DNA
<213> ORGANISM: Artificial Sequence
<220> FEATURE:
<223> OTHER INFORMATION: Primer sequence

<400> SEQUENCE: 44
caactccatc tgaacaggca gagctagaga cag                                   33

<210> SEQ ID NO 45
<211> LENGTH: 33
<212> TYPE: DNA
<213> ORGANISM: Artificial Sequence
<220> FEATURE:
<223> OTHER INFORMATION: Primer sequence

<400> SEQUENCE: 45
caactccatc taatcaggca gaagcagaga cag                                   33

<210> SEQ ID NO 46
<211> LENGTH: 33
<212> TYPE: DNA
<213> ORGANISM: Artificial Sequence
<220> FEATURE:
```

```
<223> OTHER INFORMATION: Primer sequence

<400> SEQUENCE: 46
caactccatc tatacaggca gacacagagg cag                                    33

<210> SEQ ID NO 47
<211> LENGTH: 33
<212> TYPE: DNA
<213> ORGANISM: Artificial Sequence
<220> FEATURE:
<223> OTHER INFORMATION: Primer sequence

<400> SEQUENCE: 47
caactccatc tatacaggca gaaacagaga cag                                    33

<210> SEQ ID NO 48
<211> LENGTH: 33
<212> TYPE: DNA
<213> ORGANISM: Artificial Sequence
<220> FEATURE:
<223> OTHER INFORMATION: Primer sequence

<400> SEQUENCE: 48
caactccatc tgtacaggca gagcgtgaga cag                                    33

<210> SEQ ID NO 49
<211> LENGTH: 33
<212> TYPE: DNA
<213> ORGANISM: Artificial Sequence
<220> FEATURE:
<223> OTHER INFORMATION: Primer sequence

<400> SEQUENCE: 49
caactccatc tgaacaggca gagcaagagc acg                                    33

<210> SEQ ID NO 50
<211> LENGTH: 33
<212> TYPE: DNA
<213> ORGANISM: Artificial Sequence
<220> FEATURE:
<223> OTHER INFORMATION: Primer sequence

<400> SEQUENCE: 50
caactccatc tgaacaggca gaacatgagg cag                                    33

<210> SEQ ID NO 51
<211> LENGTH: 33
<212> TYPE: DNA
<213> ORGANISM: Artificial Sequence
<220> FEATURE:
<223> OTHER INFORMATION: Primer sequence

<400> SEQUENCE: 51
caactccatc tatacaggca gacgcagaaa cag                                    33

<210> SEQ ID NO 52
<211> LENGTH: 33
<212> TYPE: DNA
<213> ORGANISM: Artificial Sequence
<220> FEATURE:
<223> OTHER INFORMATION: Primer sequence

<400> SEQUENCE: 52
caactccatc tacacaggca gaagcagagg cag                                    33

<210> SEQ ID NO 53
```

```
<211> LENGTH: 33
<212> TYPE: DNA
<213> ORGANISM: Artificial Sequence
<220> FEATURE:
<223> OTHER INFORMATION: Primer sequence

<400> SEQUENCE: 53
caactccatc tagtcaggcg gaacaagaga cag                                    33

<210> SEQ ID NO 54
<211> LENGTH: 27
<212> TYPE: DNA
<213> ORGANISM: Artificial Sequence
<220> FEATURE:
<223> OTHER INFORMATION: Primer sequence

<400> SEQUENCE: 54
tgcttcctgt gcagtaaaca acgcatg                                           27

<210> SEQ ID NO 55
<211> LENGTH: 24
<212> TYPE: DNA
<213> ORGANISM: Artificial Sequence
<220> FEATURE:
<223> OTHER INFORMATION: Primer sequence

<400> SEQUENCE: 55
gacctcctgc gcatggaaca atgc                                              24

<210> SEQ ID NO 56
<211> LENGTH: 23
<212> TYPE: DNA
<213> ORGANISM: Artificial Sequence
<220> FEATURE:
<223> OTHER INFORMATION: Primer sequence

<400> SEQUENCE: 56
cgcttcctgt gcatgaaaca atg                                               23

<210> SEQ ID NO 57
<211> LENGTH: 25
<212> TYPE: DNA
<213> ORGANISM: Artificial Sequence
<220> FEATURE:
<223> OTHER INFORMATION: Primer sequence

<400> SEQUENCE: 57
cccttcctgt atattaaaca atgcc                                             25

<210> SEQ ID NO 58
<211> LENGTH: 27
<212> TYPE: DNA
<213> ORGANISM: Artificial Sequence
<220> FEATURE:
<223> OTHER INFORMATION: Primer sequence

<400> SEQUENCE: 58
ctcctcctgt gcatgaaata atgcttg                                           27

<210> SEQ ID NO 59
<211> LENGTH: 27
<212> TYPE: DNA
<213> ORGANISM: Artificial Sequence
<220> FEATURE:
<223> OTHER INFORMATION: Primer sequence

<400> SEQUENCE: 59
```

```
gtgctgtttg tacttgcaca acaattg                                         27
```

<210> SEQ ID NO 60

<400> SEQUENCE: 60

000

<210> SEQ ID NO 61

<400> SEQUENCE: 61

000

<210> SEQ ID NO 62

<400> SEQUENCE: 62

000

<210> SEQ ID NO 63

<400> SEQUENCE: 63

000

<210> SEQ ID NO 64

<400> SEQUENCE: 64

000

<210> SEQ ID NO 65

<400> SEQUENCE: 65

000

<210> SEQ ID NO 66

<400> SEQUENCE: 66

000

<210> SEQ ID NO 67

<400> SEQUENCE: 67

000

<210> SEQ ID NO 68

<400> SEQUENCE: 68

000

<210> SEQ ID NO 69
<211> LENGTH: 149
<212> TYPE: DNA
<213> ORGANISM: Human papillomavirus

<400> SEQUENCE: 69

```
cagtgataca ggtgaagatt tggtagattt tatagtaaat gataatgatt atttaacaca      60
ggcagaaaca gagacagcac atgcgttgtt tactgcacag gaagcaaaac aacatagaga     120
tgcagtacag gttctaaaac gaagtattt                                       149
```

```
<210> SEQ ID NO 70
<211> LENGTH: 149
<212> TYPE: DNA
<213> ORGANISM: Human papillomavirus

<400> SEQUENCE: 70
aacagacaca gggtcggata tggtagattt tattgataca caaggaacat tttgtgaaca      60
ggcagagcta gagacagcac aggcattgtt ccatgcgcag gaggtccaca atgatgcaca     120
agtgttgcat gttttaaaac gaagtttgc                                       149

<210> SEQ ID NO 71
<211> LENGTH: 149
<212> TYPE: DNA
<213> ORGANISM: Human papillomavirus

<400> SEQUENCE: 71
tagtgatact ggggaggata tggttgactt tattgacaat tgtaatgtat acaacaatca      60
ggcagaagca gagacagcac aggcattgtt tcatgcacag gaagcggagg aacatgcaga     120
ggctgtgcag gttctaaaac gaagtatgt                                       149

<210> SEQ ID NO 72
<211> LENGTH: 149
<212> TYPE: DNA
<213> ORGANISM: Human papillomavirus

<400> SEQUENCE: 72
agatgacagt ggcacggatt tactagagtt tatagatgat tctatggaaa atagtataca      60
ggcagacaca gaggcagccc gggcattgtt taatatacag gaaggggagg atgatttaaa     120
tgctgtgtgt gcactaaaac gaagtttgc                                       149

<210> SEQ ID NO 73
<211> LENGTH: 149
<212> TYPE: DNA
<213> ORGANISM: Human papillomavirus

<400> SEQUENCE: 73
ctgtgacagg ggggaggata tggtggactt tataaatgat acagatatat aaacataca      60 ggcagaaaca gagacagcac aagcattatt tcatgcacag gaggagcaaa cacacaaga     120 ggctgtacag gtcctaaaac gaagtatgc                                       149

<210> SEQ ID NO 74
<211> LENGTH: 149
<212> TYPE: DNA
<213> ORGANISM: Human papillomavirus

<400> SEQUENCE: 74
aacagataca ggttcagacc tggcagactt tattgatgat tccacagata tttgtgtaca      60
ggcagagcgt gagacagcac aggtactttt acatatgcaa gaggcccaaa gggatgcaca     120
agcagtgcgt gccttaaaac gaagtatac                                       149

<210> SEQ ID NO 75
<211> LENGTH: 149
<212> TYPE: DNA
<213> ORGANISM: Human papillomavirus

<400> SEQUENCE: 75
aacagataca gggtcggata tggtagattt tattgacaca caattatcca tttgtgaaca      60
ggcagagcaa gagacagcac aggcattgtt ccatgcgcag gaagttcaga atgatgcaca     120
```

```
ggtgttgcat cttttaaaac gaagtttgc                                       149

<210> SEQ ID NO 76
<211> LENGTH: 149
<212> TYPE: DNA
<213> ORGANISM: Human papillomavirus

<400> SEQUENCE: 76
agatgataca ggatctgatt taataaactt tatagatagt gaaactagta tttgcagtca     60
ggcggaacag gagacagcac gggcgttgtt tcaggcccaa gaattacagg caaacaaaga    120
ggctgtgcat cagttaaaac gaagtttct                                      149

<210> SEQ ID NO 77
<211> LENGTH: 149
<212> TYPE: DNA
<213> ORGANISM: Human papillomavirus

<400> SEQUENCE: 77
atatgatagt ggaacagatc taatagattt tatagatgat tcaaatataa ataatgaaca     60
ggcagaacat gaggcagccc gggcattgtt taatgcacag gaaggggagg atgatttaca    120
tgctgtgtct gcagtaaaac gaagtttac                                      149

<210> SEQ ID NO 78
<211> LENGTH: 149
<212> TYPE: DNA
<213> ORGANISM: Human papillomavirus

<400> SEQUENCE: 78
ggatgaaata gatacagatt tagatggatt tatagacgat tcatatatac aaaatataca     60
ggcagacgca gaaacagtca acaattgttg caagtacaaa cagcacatgc agataaacag    120
acgttgcaaa aactaaaacg aaagtatat                                      149

<210> SEQ ID NO 79
<211> LENGTH: 149
<212> TYPE: DNA
<213> ORGANISM: Human papillomavirus

<400> SEQUENCE: 79
agacgatagt ggtacagatt taatagagtt tatagatgat tcagtacaaa gtactacaca     60
ggcagaagca gaggcagccc gagcgttgtt taatgtacag gaaggggtgg acgatataaa    120
tgctgtgtgt gcactaaaac gaagtttgc                                      149

<210> SEQ ID NO 80
<211> LENGTH: 148
<212> TYPE: DNA
<213> ORGANISM: Human papillomavirus

<400> SEQUENCE: 80
aacagataca ggttcagact tggtagattt tattgatgat accacaacaa tttgtgtaca     60
ggcagagcgc gagacagcac aggccttgtt taatgtgcag gaagcccaaa gggatgcacg    120
ggaaatgcat gttttaaaac gaagtttg                                       148

<210> SEQ ID NO 81
<211> LENGTH: 149
<212> TYPE: DNA
<213> ORGANISM: Human papillomavirus

<400> SEQUENCE: 81
```

```
aaatgataca gggtctgata taatagactt tatagataca aataacagta tttgcagtca      60
ggcggaacaa gagacagcac gggcgttgtt tcaggtccaa gaaacacagg cacacaaaga     120
ggctgcacag catctaaaac gaagttttt                                        149

<210> SEQ ID NO 82
<211> LENGTH: 149
<212> TYPE: DNA
<213> ORGANISM: Human papillomavirus

<400> SEQUENCE: 82
gaatgaaaca gatacagatg tagatggatt tatagacaat acacttataa acaatacaca      60
ggaagacagg gagacagctc aacaattatt gcaagtacaa acagcacatg cagatgcaca     120
gacgttgcaa aaactaaaac gaagtatat                                        149

<210> SEQ ID NO 83
<211> LENGTH: 149
<212> TYPE: DNA
<213> ORGANISM: Human papillomavirus

<400> SEQUENCE: 83
aacagataca ggttcagaca tggtagattt tattgatgat tctacacata tttgtataca      60
ggcagagcgt gagacagcac aggtactttt gaatatgcaa gaggcccaaa gggatgcaca     120
aagggtgcgt gccctaaaac gaagtatac                                        149

<210> SEQ ID NO 84
<211> LENGTH: 146
<212> TYPE: DNA
<213> ORGANISM: Human papillomavirus

<400> SEQUENCE: 84
aagcaccgaa tctgatttgg atgggtttat agacaatagt aatataatat ctacacaggc      60
agaaagggag acagctcagc agttgttaca tgccaaaaca cacatgcaga tacacagacg     120
ctgcagaaat taaaacgaaa gtattt                                           146

<210> SEQ ID NO 85
<211> LENGTH: 152
<212> TYPE: DNA
<213> ORGANISM: Human papillomavirus

<400> SEQUENCE: 85
aggggataca gatgagtcgg aaatgggggg attttattgat aatgcacata taccaaatat      60
atatgcacaa caggaaattg cacaggcatt gtatcagtca cagcaagcaa atgcagacaa     120
tgaggcttac gtgttctaaa acgaaagttt ac                                    152

<210> SEQ ID NO 86
<211> LENGTH: 144
<212> TYPE: DNA
<213> ORGANISM: Human papillomavirus

<400> SEQUENCE: 86
ggtggaggac agtgggtatg acatggtgga ctttattgat gacagcaata ttacacacaa      60
ttcactggaa gcacaggcat tgtttaacag gcaggaggcg acacccatt atgcgactgt     120 gcaggaccta aaacgaaagt attt                                             144

<210> SEQ ID NO 87
<211> LENGTH: 144
```

```
<212> TYPE: DNA
<213> ORGANISM: Human papillomavirus

<400> SEQUENCE: 87
ggtggaggac agtgggtatg acatggtgga ctttattgat gacagcaata ttacacacaa     60
ttcactggaa gcacaggcat tgtttaacag gcaggaggcg acacccatt atgcgactgt    120
gcaggaccta aaacgaaagt attt                                          144

<210> SEQ ID NO 88
<211> LENGTH: 144
<212> TYPE: DNA
<213> ORGANISM: Human papillomavirus

<400> SEQUENCE: 88
agtggaggat agtgggttgg atatggtgga ctttatagat gacaggccta ttacacacaa     60
ttccatggaa gcacaggcat tgttaaacga gcaggaggcg gatgctcatt atgcggctgt   120
gcaggaccta aaacgaaagt attt                                          144

<210> SEQ ID NO 89
<211> LENGTH: 150
<212> TYPE: DNA
<213> ORGANISM: Human papillomavirus

<400> SEQUENCE: 89
agaggaagat agtgggtttg atatggtaga ttttattaat aatacattag aagacagttg     60
tacagaccac agcagtgcgc aggctctgtt aaatgcacaa caagcggatg ctgatgctgc   120
tatagtgcag gagttaaaac gaaagtacat                                    150

<210> SEQ ID NO 90
<211> LENGTH: 149
<212> TYPE: DNA
<213> ORGANISM: Human papillomavirus

<400> SEQUENCE: 90
agaggatagt ggatttgata tgatagattt tattgataat agtgttgtgg cagaggaaca     60
tgtagaacta agtaatgcac aggcactttt acatgtacag cagacatgtg cagatgctgc   120
tgacctgtgc gagtaaaacg aaagtacat                                     149

<210> SEQ ID NO 91
<211> LENGTH: 147
<212> TYPE: DNA
<213> ORGANISM: Human papillomavirus

<400> SEQUENCE: 91
tgtagacgat agtgggttag atcttgtgga ttttgtagat aatagtacag taatacatac     60
aaagcaggta catgcacaag ccttattaaa taaacaacaa gcacatgcag atcaggaggc   120
agtacaggca ctaaaacgaa agctatt                                       147

<210> SEQ ID NO 92
<211> LENGTH: 144
<212> TYPE: DNA
<213> ORGANISM: Human papillomavirus

<400> SEQUENCE: 92
ggaggacagt gggcttgata tggtggactt tattgataat agtgtgtcac aggtagaggg     60
gcaggaaaat ccacaggcat tgttacatgc ccaacagctg caggcagatg tagaggcagt   120
gcaacaatta aaacgaaagt atat                                          144
```

<210> SEQ ID NO 93
<211> LENGTH: 141
<212> TYPE: DNA
<213> ORGANISM: Human papillomavirus

<400> SEQUENCE: 93
cattgacaca ggggaagacc tagtagactt catagataca aggcgccccg gggatgggca    60
ggaagtgccg cttgcgttgt tcgttcaaca aaatgcacag gatgacgctg caacggtgca   120
ggcactaaaa cgaaagtata c                                             141

<210> SEQ ID NO 94
<211> LENGTH: 149
<212> TYPE: DNA
<213> ORGANISM: Human papillomavirus

<400> SEQUENCE: 94
aacagataca ggttcagact tggcagactt tattgatgat actacagata tttgtgtaca    60
ggcagagcgc gagacagcac aggtactgta taatatgcaa gaggcccaaa gggatgcaca   120
atcagtgcgt gccttaaaac gaagtatgg                                     149

<210> SEQ ID NO 95
<211> LENGTH: 141
<212> TYPE: DNA
<213> ORGANISM: Human papillomavirus

<400> SEQUENCE: 95
tgaggacagg ggagaagatc tggtagactt tatagacaca agatccttag gggatgggca    60
ggaagtgccg ttagatttgt tcgtgcaaca aaatgcacgg gatgacgctg caaccgtgca   120
ggccctaaaa cgaaagtata c                                             141

<210> SEQ ID NO 96
<211> LENGTH: 141
<212> TYPE: DNA
<213> ORGANISM: Human papillomavirus

<400> SEQUENCE: 96
tgcagataca ggagaggatc tagtagattt catagataca cgatatccag gggatgggca    60
ggaagtgccg ttagaactgt tgttcaaca aaatgcacag gatgacgctg cagcggtgca    120
tgcactaaaa cgaaagtata t                                             141

<210> SEQ ID NO 97
<211> LENGTH: 20
<212> TYPE: DNA
<213> ORGANISM: Artificial Sequence
<220> FEATURE:
<223> OTHER INFORMATION: Primer sequence
<220> FEATURE:
<221> NAME/KEY: misc_feature
<222> LOCATION: (1)..(1)
<223> OTHER INFORMATION: C is attached to a FAM label

<400> SEQUENCE: 97
caggcagaat tagagrcagc                                                20

<210> SEQ ID NO 98
<211> LENGTH: 20
<212> TYPE: DNA
<213> ORGANISM: Artificial Sequence
<220> FEATURE:
<223> OTHER INFORMATION: Primer sequence

```
<400> SEQUENCE: 98
caggcagaat tagagrcagc                                              20

<210> SEQ ID NO 99
<211> LENGTH: 22
<212> TYPE: DNA
<213> ORGANISM: Artificial Sequence
<220> FEATURE:
<223> OTHER INFORMATION: Primer sequence

<400> SEQUENCE: 99
tccaccacaw actttcgttt ta                                           22

<210> SEQ ID NO 100
<211> LENGTH: 20
<212> TYPE: DNA
<213> ORGANISM: Artificial Sequence
<220> FEATURE:
<223> OTHER INFORMATION: Primer sequence

<400> SEQUENCE: 100
cgtccmarrg gawactgatc                                              20

<210> SEQ ID NO 101
<211> LENGTH: 20
<212> TYPE: DNA
<213> ORGANISM: Artificial Sequence
<220> FEATURE:
<223> OTHER INFORMATION: Primer sequence

<400> SEQUENCE: 101
gcmcagggwc ataayaatgg                                              20

<210> SEQ ID NO 102
<211> LENGTH: 23
<212> TYPE: DNA
<213> ORGANISM: Artificial Sequence
<220> FEATURE:
<223> OTHER INFORMATION: Primer sequence

<400> SEQUENCE: 102
tttgttactg tggtagatac tac                                          23

<210> SEQ ID NO 103
<211> LENGTH: 25
<212> TYPE: DNA
<213> ORGANISM: Artificial Sequence
<220> FEATURE:
<223> OTHER INFORMATION: Primer sequence

<400> SEQUENCE: 103
gaaaaataaa ctgtaaatca tattc                                        25
```